(12) United States Patent
Magnani et al.

(10) Patent No.: US 11,291,678 B2
(45) Date of Patent: Apr. 5, 2022

(54) METHODS FOR THE TREATMENT AND/OR PREVENTION OF CARDIOVASCULAR DISEASE BY INHIBITION OF E-SELECTIN

(71) Applicants: GlycoMimetics, Inc., Rockville, MD (US); The General Hospital Corporation, Boston, MA (US)

(72) Inventors: John L Magnani, Gaithersburg, MD (US); Matthias P Nahrendorf, Boston, MA (US)

(73) Assignees: GLYCOMIMETICS, INC, Rockville, MD (US); THE GENERAL HOSPITAL CORPORATION, Boston, MA (US)

(*) Notice: Subject to any disclaimer, the term of this patent is extended or adjusted under 35 U.S.C. 154(b) by 0 days.

(21) Appl. No.: 16/081,275

(22) PCT Filed: Mar. 1, 2017

(86) PCT No.: PCT/US2017/020091
§ 371 (c)(1),
(2) Date: Aug. 30, 2018

(87) PCT Pub. No.: WO2017/151708
PCT Pub. Date: Sep. 8, 2017

(65) Prior Publication Data
US 2019/0060339 A1 Feb. 28, 2019

Related U.S. Application Data

(60) Provisional application No. 62/302,449, filed on Mar. 2, 2016.

(51) Int. Cl.
*A61K 31/7034* (2006.01)
*A61P 9/10* (2006.01)
*A61K 31/765* (2006.01)

(52) U.S. Cl.
CPC ........ *A61K 31/7034* (2013.01); *A61K 31/765* (2013.01); *A61P 9/10* (2018.01)

(58) Field of Classification Search
CPC ...... A61K 31/7034; A61K 31/765; A61P 9/10
USPC .......................................................... 514/54
See application file for complete search history.

(56) References Cited

U.S. PATENT DOCUMENTS

| | | |
|---|---|---|
| 4,471,057 A | 9/1984 | Koprowski et al. |
| 4,851,511 A | 7/1989 | Hakomori et al. |
| 4,859,769 A | 8/1989 | Karlsson et al. |
| 4,876,199 A | 10/1989 | Hakamori |
| 4,925,796 A | 5/1990 | Bergh et al. |
| 4,946,830 A | 8/1990 | Pulverer et al. |
| 5,143,712 A | 9/1992 | Brandley et al. |
| 5,151,360 A | 9/1992 | Handa et al. |
| 5,211,937 A | 5/1993 | Brandley et al. |
| 5,268,364 A | 12/1993 | Kojima et al. |
| 5,304,640 A | 4/1994 | Lasky et al. |
| 5,352,670 A | 10/1994 | Venot et al. |
| 5,369,096 A | 11/1994 | Yamada et al. |
| 5,412,123 A | 5/1995 | Rao et al. |
| 5,444,050 A | 8/1995 | Kogan et al. |
| 5,464,778 A | 11/1995 | Cummings et al. |
| 5,464,815 A | 11/1995 | Chamow et al. |
| 5,470,843 A | 11/1995 | Stahl et al. |
| 5,484,891 A | 1/1996 | Lasky et al. |
| 5,486,536 A | 1/1996 | Ward et al. |
| 5,519,008 A | 5/1996 | Rao et al. |
| 5,527,785 A | 6/1996 | Bevilacqua et al. |
| 5,538,724 A | 7/1996 | Butcher et al. |
| 5,559,103 A | 9/1996 | Gaeta et al. |
| 5,576,305 A | 11/1996 | Ratcliffe |
| 5,580,858 A | 12/1996 | Ippolito et al. |
| 5,580,862 A | 12/1996 | Rosen et al. |
| 5,589,465 A | 12/1996 | Ishida et al. |
| 5,604,207 A | 2/1997 | DeFrees et al. |
| 5,618,785 A | 4/1997 | Heavner et al. |
| 5,622,937 A | 4/1997 | Kogan et al. |
| 5,632,991 A | 5/1997 | Gimbrone, Jr. |
| 5,639,734 A | 6/1997 | Esko et al. |
| 5,646,123 A | 7/1997 | Ippolito et al. |
| 5,646,248 A | 7/1997 | Sawada et al. |
| 5,648,344 A | 7/1997 | Brandley et al. |
| 5,654,282 A | 8/1997 | Tang et al. |
| 5,654,412 A | 8/1997 | Srivastava et al. |
| 5,658,880 A | 8/1997 | Dasgupta et al. |
| 5,663,151 A | 9/1997 | Martel et al. |
| 5,679,321 A | 10/1997 | Dasgupta et al. |
| 5,679,644 A | 10/1997 | Rao et al. |

(Continued)

FOREIGN PATENT DOCUMENTS

| | | |
|---|---|---|
| DE | 2434953 | 2/1975 |
| EP | 319253 A2 | 6/1989 |

(Continued)

OTHER PUBLICATIONS

Falk (Am J Cardiol 1995;75:5B-11B).*
Robbins et al. (Circulation. 2012;125:364-374).*
Khrenov et al. (Trends Cardiovasc Med 2002; vol. 12, No. 7: 317-324).*
AAPC (Myocardial Infarction (MI) Quick Reference, 2013).*
Brieger et al. (Am J Cardiol 1998;81:282-287).*
Abraham, W.M. et al., "Selectin Blockade Prevents Antigen-induced Late Bronchial Response and Airway Hyperresponsiveness in Allergic Sheep," Am J. Respir Crit Care Med. 159: 1205-1214, 1999.
Acord, J. et al., "A rapid microplate method for quantifying inhibition of bacterial adhesion to eukaryotic cells," Journal of Microbiological Methods 60: 55-62, 2005.
Adams, E. W. et al., "Oligosaccharide and Glycoprotein Microarrays as Tools in HIV Glycobiology: Glycan-Dependent gp120/Protein Interactions," Chemistry & Biology 11:875-881, Jun. 2004.

(Continued)

*Primary Examiner* — Shaojia A Jiang
*Assistant Examiner* — Michael C Henry
(74) *Attorney, Agent, or Firm* — Finnegan, Henderson, Farabow, Garrett & Dunner LLP

(57) ABSTRACT

New methods for treating and/or preventing cardiovascular disease including, for example, myocardial infarction and atherosclerosis, by the use of at least one E-selectin inhibitor and compositions comprising the same are disclosed.

23 Claims, 6 Drawing Sheets

(56) References Cited

U.S. PATENT DOCUMENTS

| | | |
|---|---|---|
| 5,686,426 A | 11/1997 | Martel et al. |
| 5,693,621 A | 12/1997 | Toepfer et al. |
| 5,695,752 A | 12/1997 | Rosen et al. |
| 5,710,023 A | 1/1998 | Collins et al. |
| 5,710,123 A | 1/1998 | Heavner et al. |
| 5,723,583 A | 3/1998 | Seed et al. |
| 5,728,685 A | 3/1998 | Abbas et al. |
| 5,739,300 A | 4/1998 | Toepfer et al. |
| 5,747,463 A | 5/1998 | Marinier et al. |
| 5,750,508 A | 5/1998 | Dasgupta et al. |
| 5,753,617 A | 5/1998 | Heavner et al. |
| 5,753,631 A | 5/1998 | Paulson et al. |
| 5,763,413 A | 6/1998 | Numata et al. |
| 5,763,582 A | 6/1998 | Rao et al. |
| 5,789,385 A | 8/1998 | Anderson et al. |
| 5,789,573 A | 8/1998 | Baker et al. |
| 5,795,958 A | 8/1998 | Rao et al. |
| 5,811,404 A | 9/1998 | De Frees et al. |
| 5,811,405 A | 9/1998 | Toepfer et al. |
| 5,817,742 A | 10/1998 | Toepfer et al. |
| 5,817,807 A | 10/1998 | Bridger et al. |
| 5,827,817 A | 10/1998 | Larsen et al. |
| 5,827,837 A | 10/1998 | Bevilacqua et al. |
| 5,830,871 A | 11/1998 | Wong et al. |
| 5,837,689 A | 11/1998 | Anderson et al. |
| 5,837,690 A | 11/1998 | Rao et al. |
| 5,840,679 A | 11/1998 | Larsen et al. |
| 5,854,218 A | 12/1998 | DeFrees |
| 5,856,300 A | 1/1999 | Rittershaus et al. |
| 5,858,983 A | 1/1999 | Seed et al. |
| 5,858,994 A | 1/1999 | Kretzschmar et al. |
| 5,880,091 A | 3/1999 | Cummings et al. |
| 5,916,910 A | 6/1999 | Lai |
| 5,919,768 A | 7/1999 | Korgan et al. |
| 5,919,769 A | 7/1999 | Tsukida et al. |
| 5,962,422 A | 10/1999 | Nagy et al. |
| 5,976,540 A | 11/1999 | Rittershaus et al. |
| 5,977,080 A | 11/1999 | Rosen et al. |
| 5,985,852 A | 11/1999 | Nagy et al. |
| 5,994,402 A | 11/1999 | Rotstein et al. |
| 6,001,819 A | 12/1999 | Simon et al. |
| 6,001,988 A | 12/1999 | Parma et al. |
| 6,033,665 A | 3/2000 | Yednock et al. |
| 6,037,333 A | 3/2000 | Panjwani |
| 6,043,348 A | 3/2000 | Lawman et al. |
| 6,110,897 A | 8/2000 | Unverzagt et al. |
| 6,111,065 A | 8/2000 | Heavner et al. |
| 6,120,751 A | 9/2000 | Unger |
| 6,121,233 A | 9/2000 | Magnani et al. |
| 6,124,267 A | 9/2000 | McEver et al. |
| 6,133,239 A | 10/2000 | Handa et al. |
| 6,133,240 A | 10/2000 | Taylor et al. |
| 6,136,790 A | 10/2000 | Toepfer et al. |
| 6,169,077 B1 | 1/2001 | Oehrlein |
| 6,177,547 B1 | 1/2001 | Cummings et al. |
| 6,187,754 B1 | 2/2001 | Oehrlein |
| 6,193,973 B1 | 2/2001 | Tuttle |
| 6,193,979 B1 | 2/2001 | Rittershaus et al. |
| 6,197,752 B1 | 3/2001 | Schmidt et al. |
| 6,225,071 B1 | 5/2001 | Cummings et al. |
| 6,235,309 B1 | 5/2001 | Nagy et al. |
| 6,280,932 B1 | 8/2001 | Parma et al. |
| 6,287,556 B1 | 9/2001 | Portnoy et al. |
| 6,309,639 B1 | 10/2001 | Cummings et al. |
| 6,372,712 B1 | 4/2002 | Briesewitz |
| 6,387,884 B1 | 5/2002 | Magnani et al. |
| 6,391,857 B1 | 5/2002 | Magnani et al. |
| 6,407,135 B1 | 6/2002 | Lai et al. |
| 6,465,434 B1 | 10/2002 | Magnani et al. |
| 6,492,332 B1 | 10/2002 | Demopulos et al. |
| 6,503,885 B1 | 1/2003 | Kiso et al. |
| 6,506,770 B1 | 1/2003 | Bridger et al. |
| 6,515,117 B2 | 2/2003 | Ellsworth et al. |
| 6,528,487 B1 | 3/2003 | Heavner et al. |
| 6,569,998 B2 | 5/2003 | Cummings et al. |
| 6,592,872 B1 | 7/2003 | Klimpel et al. |
| 6,683,056 B2 | 1/2004 | Washburn et al. |
| 6,756,391 B2 | 6/2004 | Bridger et al. |
| 6,844,125 B2 | 1/2005 | Bistrup et al. |
| 6,872,714 B1 | 3/2005 | Schols |
| 6,875,738 B1 | 4/2005 | Clark-Lewis et al. |
| 6,887,842 B1 | 5/2005 | Briesewitz |
| 6,921,531 B2 | 7/2005 | Briesewitz |
| 6,943,239 B2 | 9/2005 | Holgersson et al. |
| 6,967,093 B2 | 11/2005 | Bistrup et al. |
| 7,060,685 B2 | 6/2006 | Magnani et al. |
| 7,087,212 B2 | 8/2006 | Cantrell et al. |
| 7,160,872 B2 | 1/2007 | Bridger et al. |
| 7,226,949 B2 | 6/2007 | Crooks et al. |
| 7,300,656 B2 | 11/2007 | Ashkenazi et al. |
| 7,361,644 B2 | 4/2008 | Magnani et al. |
| 7,390,784 B2 | 6/2008 | Briesowitz |
| 7,414,065 B2 | 8/2008 | Bridger et al. |
| 7,422,733 B2 | 9/2008 | Ranganathan et al. |
| 7,449,176 B2 | 11/2008 | Ashkenazi et al. |
| 7,517,980 B2 | 4/2009 | Magnani et al. |
| 7,563,760 B2 | 7/2009 | Larsen et al. |
| 7,709,486 B2 | 5/2010 | Bridger et al. |
| 7,728,117 B2 | 6/2010 | Magnani et al. |
| 7,741,312 B2 | 6/2010 | Magnani et al. |
| 7,951,816 B2 | 5/2011 | Kokubo et al. |
| 7,964,569 B2 | 6/2011 | Ernst et al. |
| 7,989,601 B2 | 8/2011 | Magnani et al. |
| 8,026,222 B2 | 9/2011 | Magnani et al. |
| 8,039,442 B2 | 10/2011 | Magnani |
| 8,258,290 B2 | 9/2012 | Magnani et al. |
| 8,361,975 B2 | 1/2013 | Magnani |
| 8,410,066 B2 | 4/2013 | Magnani |
| 8,518,896 B2 | 8/2013 | Magnani et al. |
| 8,530,448 B2 | 9/2013 | Magnani et al. |
| 8,633,303 B2 | 1/2014 | Magnani et al. |
| RE44,778 E | 2/2014 | Magnani et al. |
| 8,895,510 B2 | 11/2014 | Magnani |
| 8,921,328 B2 | 12/2014 | Ernst et al. |
| 9,109,002 B2 | 8/2015 | Magnani et al. |
| 9,254,322 B2 | 2/2016 | Levesque et al. |
| 9,486,497 B2 | 11/2016 | Levesque et al. |
| 9,534,009 B2 | 1/2017 | Magnani |
| 9,796,745 B2 | 10/2017 | Magnani et al. |
| 9,867,841 B2 | 1/2018 | Magnani |
| 2001/0046970 A1 | 11/2001 | Nagy et al. |
| 2001/0051370 A1 | 12/2001 | Bistrup et al. |
| 2002/0031508 A1 | 3/2002 | Wagner et al. |
| 2002/0040008 A1 | 4/2002 | Wagner et al. |
| 2002/0086356 A1 | 7/2002 | Tuschl et al. |
| 2002/0128225 A1 | 9/2002 | Liu et al. |
| 2002/0132220 A1 | 9/2002 | Berens et al. |
| 2002/0155429 A1 | 10/2002 | Allaway et al. |
| 2002/0164336 A1 | 11/2002 | Harrison et al. |
| 2002/0164748 A1 | 11/2002 | Bistrup et al. |
| 2002/0165178 A1 | 11/2002 | Schetter et al. |
| 2002/0168366 A1 | 11/2002 | Stewart et al. |
| 2003/0012787 A1 | 1/2003 | Ashkenazi et al. |
| 2003/0012790 A1 | 1/2003 | Ashkenazi et al. |
| 2003/0018181 A1 | 1/2003 | Larsen et al. |
| 2003/0036560 A1 | 2/2003 | Sonis et al. |
| 2003/0039683 A1 | 2/2003 | Cantrell et al. |
| 2003/0073632 A1 | 4/2003 | Ciacci et al. |
| 2003/0211078 A1 | 11/2003 | Heavner |
| 2004/0067220 A1 | 4/2004 | Sykes |
| 2004/0072796 A1 | 4/2004 | Embury et al. |
| 2004/0096396 A1 | 5/2004 | Magnani et al. |
| 2004/0097403 A1 | 5/2004 | Ranganathan et al. |
| 2004/0219158 A1 | 11/2004 | Magnani |
| 2005/0112124 A1 | 5/2005 | Frenette et al. |
| 2005/0181987 A1 | 8/2005 | Blaszczyk-Thurin et al. |
| 2005/0187171 A1 | 8/2005 | Magnani et al. |
| 2005/0214283 A1 | 9/2005 | Sackstein et al. |
| 2006/0194745 A1 | 8/2006 | Magnani et al. |
| 2006/0217303 A1 | 9/2006 | Kriegler |
| 2006/0264451 A1 | 11/2006 | Shim et al. |
| 2006/0287253 A1 | 12/2006 | Kriegler et al. |
| 2007/0021378 A1 | 1/2007 | Varki et al. |
| 2007/0054870 A1 | 3/2007 | Magnani et al. |

(56) References Cited

U.S. PATENT DOCUMENTS

| | | | |
|---|---|---|---|
| 2007/0054930 A1 | 3/2007 | Shim et al. |
| 2007/0213278 A1 | 9/2007 | Wong et al. |
| 2008/0025992 A1 | 1/2008 | Fabene et al. |
| 2008/0112955 A1 | 5/2008 | Embury et al. |
| 2008/0161546 A1 | 7/2008 | Ernst et al. |
| 2008/0200406 A1 | 8/2008 | Magnani |
| 2008/0227799 A1 | 9/2008 | Liotta et al. |
| 2008/0300220 A1 | 12/2008 | Ranganathan et al. |
| 2008/0306098 A1 | 12/2008 | Mutz et al. |
| 2009/0036386 A1 | 2/2009 | Magnani et al. |
| 2009/0053198 A1 | 2/2009 | Sackstein |
| 2009/0054334 A1 | 2/2009 | Mutz et al. |
| 2009/0175792 A1 | 7/2009 | Magnani et al. |
| 2009/0176717 A1 | 7/2009 | Magnani |
| 2009/0253646 A1 | 10/2009 | Magnani |
| 2009/0312278 A1 | 12/2009 | Magnani et al. |
| 2010/0145032 A1 | 6/2010 | Laine et al. |
| 2010/0215575 A1 | 8/2010 | O'Neill et al. |
| 2010/0240773 A1 | 9/2010 | Korzekwa et al. |
| 2010/0292095 A1 | 11/2010 | Laukkanen et al. |
| 2010/0303766 A1 | 12/2010 | Miyaji et al. |
| 2010/0311105 A1 | 12/2010 | Lu et al. |
| 2011/0002881 A1 | 1/2011 | Levesque et al. |
| 2011/0020270 A1 | 1/2011 | Levesque et al. |
| 2011/0142856 A1 | 6/2011 | Kokubo et al. |
| 2011/0229409 A1 | 9/2011 | Ranganathan et al. |
| 2011/0245265 A1 | 10/2011 | Zuk et al. |
| 2011/0251148 A1 | 10/2011 | Magnani et al. |
| 2011/0257380 A1 | 10/2011 | Ernst et al. |
| 2012/0093782 A1 | 4/2012 | Grove et al. |
| 2012/0129712 A1 | 5/2012 | Satomaa et al. |
| 2012/0202762 A1 | 8/2012 | Magnani |
| 2012/0258043 A1 | 10/2012 | Ranganathan et al. |
| 2012/0329755 A1 | 12/2012 | Magnani et al. |
| 2013/0184229 A1 | 7/2013 | Magnani et al. |
| 2013/0261070 A1 | 10/2013 | Magnani et al. |
| 2013/0281646 A1 | 10/2013 | Korzekwa et al. |
| 2013/0331350 A1 | 12/2013 | Ernst et al. |
| 2014/0073594 A1 | 3/2014 | Magnani et al. |
| 2014/0178303 A1 | 6/2014 | Magnani et al. |
| 2015/0051164 A1 | 2/2015 | Magnani |
| 2015/0110808 A1 | 4/2015 | Magnani et al. |
| 2015/0284420 A1 | 10/2015 | Magnani et al. |
| 2016/0145290 A1 | 5/2016 | Magnani et al. |
| 2016/0184339 A1 | 6/2016 | Magnani |
| 2016/0193294 A1 | 7/2016 | Magnani et al. |
| 2016/0243145 A1 | 8/2016 | Magnani et al. |
| 2016/0289257 A1 | 10/2016 | Magnani et al. |
| 2016/0333043 A1 | 11/2016 | Magnani et al. |

FOREIGN PATENT DOCUMENTS

| | | | |
|---|---|---|---|
| EP | 381310 A1 | 8/1990 |
| EP | 408859 B1 | 1/1991 |
| EP | 671407 A2 | 9/1995 |
| EP | 0 867 722 | 9/1998 |
| JP | 06-0306092 | 11/1994 |
| JP | 9-176047 | 7/1997 |
| JP | 2002-520323 | 7/2002 |
| JP | 2004-518704 | 6/2004 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/25043 | 11/1994 |
| WO | WO 94/26760 | 11/1994 |
| WO | WO 94/29477 | 12/1994 |
| WO | WO 95/00527 | 1/1995 |
| WO | WO 95/03059 | 2/1995 |
| WO | WO 95/29681 | 11/1995 |
| WO | WO 95/31210 | 11/1995 |
| WO | WO 96/20204 | 7/1996 |
| WO | WO 96/25418 | 8/1996 |
| WO | WO 96/26950 | 9/1996 |
| WO | WO 96/40942 | 12/1996 |
| WO | WO 97/01355 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 2/1998 |
| WO | WO 98/13058 | 4/1998 |
| WO | WO 98/046771 | 10/1998 |
| WO | WO 99/42130 | 8/1999 |
| WO | WO 99/43353 | 9/1999 |
| WO | WO 99/43356 | 9/1999 |
| WO | WO 99/065712 | 12/1999 |
| WO | WO 00/02870 | 1/2000 |
| WO | WO 00/050032 | 8/2000 |
| WO | WO 00/066112 | 11/2000 |
| WO | WO 01/89564 | 11/2001 |
| WO | WO 02/22820 | 3/2002 |
| WO | WO 02/062810 | 8/2002 |
| WO | WO 03/032925 | 4/2003 |
| WO | WO 03/055876 | 7/2003 |
| WO | WO 03/088980 | 10/2003 |
| WO | WO 03/097658 | 11/2003 |
| WO | WO 04/004636 | 1/2004 |
| WO | WO 04/033663 | 4/2004 |
| WO | WO 04/058304 | 7/2004 |
| WO | WO 04/094619 | 11/2004 |
| WO | WO 05/016349 | 2/2005 |
| WO | WO 05/046597 | 5/2005 |
| WO | WO 05/051920 | 6/2005 |
| WO | WO 05/054264 | 6/2005 |
| WO | WO 05/058934 | 6/2005 |
| WO | WO 05/085219 | 9/2005 |
| WO | WO 05/116088 | 12/2005 |
| WO | WO 06/017180 | 2/2006 |
| WO | WO 06/022454 | 3/2006 |
| WO | WO 06/062946 | 6/2006 |
| WO | WO 06/074426 | 7/2006 |
| WO | WO 06/074428 | 7/2006 |
| WO | WO 06/089106 | 8/2006 |
| WO | WO 06/127906 | 11/2006 |
| WO | WO 07/021721 | 2/2007 |
| WO | WO 07/022089 | 2/2007 |
| WO | WO 07/022385 | 2/2007 |
| WO | WO 07/028050 | 3/2007 |
| WO | WO 07/033329 | 3/2007 |
| WO | WO 08/008852 | 1/2008 |
| WO | WO 08/008854 | 1/2008 |
| WO | WO 08/011094 | 1/2008 |
| WO | WO 08/060378 | 5/2008 |
| WO | WO 08/100453 | 8/2008 |
| WO | WO 08/109154 | 9/2008 |
| WO | WO 09/011889 | 1/2009 |
| WO | WO 09/073911 | 6/2009 |
| WO | WO 09/073916 | 6/2009 |
| WO | WO 09/126556 | 10/2009 |
| WO | WO 09/152245 | 12/2009 |
| WO | WO 10/126888 | 11/2010 |
| WO | WO 12/037034 | 3/2012 |
| WO | WO 12/045913 | 4/2012 |
| WO | WO 12/061662 | 5/2012 |
| WO | WO 12/151576 | 11/2012 |
| WO | WO 13/096926 | 6/2013 |
| WO | WO 14/070991 | 5/2014 |
| WO | WO 14/149837 | 9/2014 |
| WO | WO 15/048616 | 4/2015 |
| WO | WO 15/109049 | 7/2015 |
| WO | WO 16/089872 | 6/2016 |
| WO | WO 16/164394 | 10/2016 |
| WO | WO 17/095904 | 6/2017 |

OTHER PUBLICATIONS

Aggoune et al., "The Vascular Niche Is Involved in Regulating Leukemic Stem Cells in Murine Chronic Myelogenous Leukemia" Blood, 124(21):516, Dec. 6, 2014.

Aggouneet al., "The vascular niche is involved in regulating leukemic stem cells in murine chronic myelogenous leukemia," Proceedings of the 56th Annual Meeting of the American Society of

(56) References Cited

OTHER PUBLICATIONS

Hematology, Abstract #516 Oral Presentation, Dec. 8, 2014, San Francisco, CA.
Alessandro et al., "Multiple Myeloma Cells Express Functional E-Selectin Ligands Which Can be Inhibited Both in vitro and in vivo Leading to Prolongation of Survival in a Murine Transplant Model," Blood, Dec. 6, 2014, XP055349837, 56th Annual Meeting of the American Society of Hematology, Dec. 6-9, 2014, San Francisco, CA.
Alessandro, et al., "Role of S128R polymorphism of E-selectin in colon metastasis formation," Int. J. Cancer, 121(3): 528-535 (2007).
Ali, M., et al., "Polymers bearing sLex-mimetics are superior inhibitors of E-selectin-dependent leukocyte rolling in vivo", The FASEB Journal 18(1), (2004), 152-154.
Alousi, A., et al., "Reduced-Intensity Conditioning Allogeneic Hematopoietic Stem Cell Transplantation", Clinical Advances in Hematoloav & Oncoloav. 5(7), (2007), 560-570.
Angelini et al., "E-Selectin Antagonist GMI-1271 Shows a Favorable Safety, PK and Bleeding Profile in Phase I Studies of Healthy Volunteers," Blood, 128(22), Abstract #3826, Dec. 6, 2014.
Angelini et al., "E-selectin Antagonist GMI-1271 Shows a Favorable Safety, PK and Bleeding Profile in Phase I Studies of Healthy Volunteers," Proceedings of the 56th Annual Meeting of the American Society of Hematology, Abstract #3826 Poster Presentation, Dec. 8, 2014, San Francisco, CA.
Arakaki, R. et al., "T134, a Small-Molecule CXCR4 Inhibitor, Has No Cross-Drug Resistance with AMD3100, a CXCR4 Antagonist with a Different Structure," Journal of Virology 73(2):1719-1723, Feb. 1999.
Aref et al., "L and E Selectins in Acute Myeloid Leukemia: Expression, Clinical Relevance and Relation to Patient Outcome," Hematology, 7(2), 83-87, 2002.
Arshad, S. et al., "Primary prevention of asthma and atopy during childhood by allergen avoidance in infacny: a randomised controlled study," Thorax., 58:489-493 (2003).
Arshad, S. et al., "Primary prevention of asthma and allergy," J. Allergy Clin. Immunol., 116: 3-14 (2005).
Astronomo, R.D. et al., "A Glycoconjugate Antigen Based on the Recognition Motif of a Broadly Neutralizing Human Immunodeficiency Virus Antibody, 2G12, Is Immunogenic but Elicits Antibodies Unable to Bind to the Self Glycans of gp120," Journal of Virology 82(13):6359-6368, Jul. 2008.
Azab et al., "P-selectin Glycoprotein Ligand Regulates the Interaction of Multiple Myeloma Cells with the Bone Marrow Microenvironment", Blood, 119(6),1468-1478, Nov. 16, 2011.
Azab et al., "Role of Selectins in the Pathogenesis of Multiple Myeloma", J Clin Oncol, 27(15s):Absrt 11103, 2009.
Azab et al., "Role of Selectins in the Pathogenesis of Multiple Myeloma", ASCO Annual Meeting 2009, Poster #11103, May 2009.
Baeckstrom et al., "Purification and Characterization of a Membrane-bound and a Secreted Mucin-type Glycoprotein Carrying the Carcinoma-associated Sialyl-Le.sup.a Epitope on Distinct Core Proteins," J. Biol. Chem. 266(32):21537-21547, 1991.
Banteli, R. et al., "Potent E-Selectin Antagonists," Helvetica Chimica Acta 83(11): 2893-2907, 2000.
Banteli et al., "Synthesis of sialyl lewisx mimics. Modifications of the 6-position of galactose," Bioorganic & Medicinal Chemistry Letters, 11(4): 459-462 (2001).
Barasch et al., "Palifermin for Management of Treatment-Induced Oral Mucositis in Cancer Patients", Biologies: Targets & Therapy, 3:111-116, 2009.
Barnes, P. et al., "How do corticosteroids work in asthma?" Ann. Intern. Med., 139: 359-370 (2003).
Barthel et al., "Targeting selectins and selectin ligands in inflammation and cancer," Expert Opinion Therapeutic Targets, 11(11), 1473-1491, 2007.
Bastin, R.. et al,"Salt Selection and Optimisation Procedures for Pharmaceutical New Chemical Entities" Organic Process Research & Development (2000), vol. 4, pp. 427-435.

Bedard et al., "Expert Opinion: Selectin Inhibitors: A Patent Review," Rights Link, 20(6):781-793, 2010.
Belcher, J.D. et al., "Activated monocytes in sickle cell disease: potential role in the activation of vascular endothelium and vaso-occlusion," Blood 96(7):2451-2459, Oct. 1, 2000.
Belcher, J.D. et al., "Inflammatory response in transgenic mouse models of human sickle cell anemia," Blood 96(11)Pt. 1 :600a, Abstract #2574, Nov. 16, 2000.
Bennett, C. F., et al., "Inhibition of Endothelial Cell Adhesion Molecule Expression with Antisense Oligonucleotides", Journal of Immunoloav. 152(7), (1994), 3530-3540.
Berg et al., "A Carbohydrate Domain Common to Both Sialyl Le.sup.a and Sialyl Le.sup.x Is Recognized by the Endothelial Cell Leukocyte Adhesion Molecule ELAM-1," J. Biol. Chem. 266(23):14869-14872, 1991.
Berg et al., "The Cutaneous Lymphocyte Antigen Is a Skin Lymphocyte Homing Receptor for the Vascular Lectin Endothelial Cell-Leukocyte Adhesion Molecule 1," J. Exp. Med. 174:1461-1466, 1991.
Berger et al., "Adoptive transfer of effector CD8+ T cells derived from central memory cells establishes persistent T cell memory in primates." J. Clin. Invest. 118(1):294-305 (2008).
Bevilacqua, et al., "Endothelial-leukocyte adhesion molecules in human disease," Ann. Rev. Med., 45: 361-378 (1994).
Bhaskar, V. et al. "E-selectin Up-regulation Allows for Targeted Drug Delivery in Prostrate Cancer," Cancer Research, 63: 6387-6394 (Oct. 2003).
Bird et al., "Oligosaccharides Containing Fucose Linked .alpha.(1-3) and .alpha.(1-4) to N-Acetylglucosamine Cause Decompaction of Mouse Morulae," Devel. Biol. 104:449-460, 1984.
Bjercke,"Rational Design and Synthesis of Oligosaccharide Mimetics: Selectin Antagonists as Cell Adhesion Inhibitors," Abstracts of Papers, 210th ACS National Meeting, American Chemical Society, Chicago, IL, Aug. 20-24, 1995, MEDI-18.
Blanc-Muesser et al., "Syntheses Stereoselective de 1-Thioglycosides," Carbohydrate Research 67:305-328, 1978, and English Translation.
Bochner, B. et al., "Glycan array screening reveals a candidate ligand for Siglec-8," Journal of Biological Chemistry, 280(6): 4307-4312 (2005).
Bock, K. et al., "Conformations in Solution of a, a-Trehalose, a-D-Glucopyranosyl a-D-Mannopyranoside, and Their 1-Thioglycosyl Analogs, and a Tentative Correlation of Their Behaviour with Respect to the Enzyme Trehalase," European Journal of Biochemistry, 131:595-600, 1983.
Bogden, A. E., et al., "Amelioration of Chemotherapy-Induced Toxicity by Cotreatment with AcSDKP, a Tetrapeptide Inhibitor of Hematopoietic Stem Cell Proliferation", Annals New York Academv of Sciences. 628, (1991), 126-139.
Borsig et al., "Synergistic effects of L- and P-selectin in facilitating tumor metastasis can involve non-mucin ligands and implicate leukocytes ad enhancers of metastasis," Proceedings of the National Academy of Sciences, 99(4), 2193-2198, 2002.
Bowen et al., "Characterization of a Human Homologue of the Murine Peripheral Lymph Node Homing Receptor," Journal of Cell Biology, 109:421-427, 1989.
Bradford, G. B., et al., "Quiescence, cycling, and turnover in the primitive hematopoietic stem cell compartment", Experimental Hematoloav. 25, (1997), 445-453.
Brandley et al., "Carbohydrate Ligands of LEC Cell Adhesion Molecules," Cell, 63:861-863, 1990.
Breems et al., "Prognostic Index for Adult Patients With Acute Myeloid Leukemia in First Relapse," Journal of Clinical Oncology, 23(9( ), 1969-1978, 2005.
Bridger, GJ et al. "Synthesis and Structure—Activity Relationships of Phenylenebis(methylene)—Linked Bis-Tetraazamacrocycles That Inhibit HIV Replication. Effects of Macrocyclic Ring Size and Substituents on the Aromatic Linker," J. Med. Chem., 38: 366-378 (1995).
Brodt et al., "Liver endothelial E-selectin mediates carcinoma cell adhesion and promotes liver metastasis," Int. J. Cancer, 71(4): 612-619 (1997).

(56) References Cited

OTHER PUBLICATIONS

Broquet et al., "Effect of Desipramine on a Glycoprotein Sialyltransferase Activity in C6 Cultured Glioma Cells," J. Neurochem., 54:388-394, 1990.
Burkhardt, K., et al., "The Significance of Adhesion Molecules in Nephrology", Artificial Oraans 20(5), (1996), 433-436.
Calarese, D. A. et al., "Antibody Domain Exchange is and Immunological Solution to Carbohydrate Cluster Recognition," Science 300:2065-2071, Jun. 2003.
Calarese, D. A. et al., "Dissection of the Carbohydrate Specificity of the Broadly Neutralizing Anti-HIV-1 Antibody 2G12," Proceedings of the National Academy of Sciences 102(38):13372-13377, Sep. 2005.
Cao, X. et al., "Defective Lymphoid Development in Mice Lacking Expression of the Common Cytokine Receptor Y Chain," Immunity, 2:223-238, Mar. 1995.
Ceder, O. et al., "On the Absolute Configuration of 3-Cyclohexene-I-carboxylic Acid," Acta Chemica Scandivavica, 24(8):2693-2698, 1970.
Chang et al., "Effects of Pan-Selectin Antagonist GMI-1070 on the Treatment of Vaso-Occlusion in Sickle Cell Mice", Blood, 112(11), Abstract #535, Nov. 2008.
Chang, J. et al. "GMI-1070, a novel pan-selectin antagonist, reverses acute vascular occlusions in sickle cell mice," Blood, 116(10): 1779-1786 (Sep. 2010).
Chase et al., "E-Selectin Ligands as Mechanosensitive Receptors on Neutrophils in Health and Disease", Annals of Biomedical Engineering, 40(4), pp. 849-899, Apr. 2012.
Chemical Abstracts (STN), Accession No. 1997:584307, Jul. 8, 1997.
Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML," Proceedings of the 54$^{th}$ Annual Meeting of the American Society of Hematology, Abstract #4092, Poster Presentation, Dec. 10, 2012, San Diego, CA.
Chien et al., "Adhesion of Acute Myeloid Leukemia Blasts to E-Selectin in the Vascular Niche Enhances Their Survival by Mechanisms Such as Wnt Activation", Blood, 122(21):61, Nov. 15, 2013.
Chien et al., "579 Novel Dual E-Selectin-CXCR4 Inhibitors Mobilize Human Acute Myeloid Leukemia (AML) Cells in the NODscid IL2Rγc-/- Xenograft and Confer Susceptibility to Cytarabine," Blood, 118(21) Abstract #579, Oral, Nov. 18, 2011.
Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML", Blood, 120(21), Abstract #4092, Nov. 16, 2012.
Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML", 2012 ASH Annual Meeting, Poster #54715, Dec. 10, 2012.
Chien et al., "Novel Dual E-Selectin-CXCR4 Inhibitors Mobilize Human Acute Myeloid Leukemia (AML) Cells in the NODscid IL2R{gamma}c-/- Xenograft and Confer Susceptibility to Cytarabine", Blood, 118(21), Abstract #579, Nov. 18, 2011.
Childs et al. ,"High-molecular-weight glycoproteins are the major carriers of the carbohydrate differentiation antigens I, I and SSEA-1 of mouse teratocarcinoma cells," Biochem. J., 215:491-503 (1983).
Choi, S. et al., "Synthetic Multivalent Molecules: Concepts and Biomedical Applications," Wiley-Interscience, p. xxi-xxvi, 1-17, 2004.
Christianson, S.W. et al.,"Enhanced Human CD4+ T Cell Engraftment in β2-Microglobulin-Deficient NOD-scid Mice," The Journal of Immunology, 158:3578-3586 (1997).
Cleophax, J. et al., "A chiral synthesis of D-(+)-2,6-dideoxystreptamine and its microbial incorporation into novel antibodies," Journal of the American Chemical Society, 98 (22): 7110-7112 (Oct. 27, 1976).

Collier, et al., "Membrane translocation by anthrax toxin," Molecular Aspects of Medicine, 30(6): 413-422 (Dec. 1, 2009).
Corral et al., "Requirements for Sialic Acid on Neutrophils in a GMP-140 (PADGEM) Mediated Adhesive Interaction with Activated Platelets," Biochem. Biophys. Res. Commun., 172:1349-1356, (1990).
Corson, Timothy W. et al., "Design and Applications of Bifunctional Small Molecules: Why Two Heads Are Better Than One," ACS Chemical Biology 3(11):677-692, Nov. 2008.
Cottler-Fox, M.H. et al., "Stem Cell Mobilization," Amer. Sci. Hematology, 419-437, (2003).
Crawford et al., "AMD070, a CXCR4 Chemokine Receptor Antagonist: Practical Large-Scale Laboratory Synthesis," Org. Process Res. Devel. 12:823-830, 2008.
Cumpstey, I. et al. "C2-Symmetrical Thiodigalactoside Bis-Benzamido Derivatives as High-Affinity Inhibitors of Galectin-3: Efficient Lectin Inhibition through Double Arginine-Arene Interactions," Angew Chem., 117:5240-5242 (2005).
Dagia, Nilesh et al., "G-CSF induces E-selecting ligand expression on human myeloid cells," Nature Medicine, 12(10): 1185-90, Oct. 1, 2006.
Daoudii, Jean-Michel et al., "New bicyclam-GalCer analogue conjugates: synthesis and in vitro anti-HIV activity," Bioorg. & Med. Chem. Letters 14:495-498, 2004.
Datta et al., "Isolation and purification of trehalose 6-mono- and 6,6'-di-corynomycolates from Cornyebacterium matruchotii. Structural characterization of .sup.1H NMR," Carbohydrate Research 245: 151-158, 1993.
De Castro et al., "Effects of GMI-1070, a Pan-Selectin Inhibitor, on Pain Intensity and Opioid Utilization in Sickle Cell Disease", Blood, 122(21):775, Nov. 15, 2013.
De Clercq, Erik, "The bicyclam AMD3100 story," Nat. Rev. Drug Disc. 2:581-587, Jul. 2003.
DeAngelo, "A Phase I/II Study of GMI-1271, a Novel ESelectin Antagonist, in Combination with Induction Chemotherapy in Relapsed/Refractory and Elderly Previously Untreated Acute Myeloid Leukemia; Results to Date," Blood, 128(22), Abstract #4049, Dec. 2, 2016.
Definition of allogenic. Medline Plus-Merriam-Webster Medical Dictionary (last accessed Jun. 3, 2013).
Definition of syngeneic. Medline Plus-Merriam-Webster Medical Dictionary (last accessed Jun. 3, 2013).
Definition of xenogeneic. Medline Plus-Merriam-Webster Medical Dictionary (last accessed Jun. 3, 2013).
Demain et al. "Natural products for cancer chemotherapy," Microbio. Biotechnol. 4(6): 687-699, 2011.
Devata et al., First in Human Phase 1 Single Dose Escalation Studies of the E-Selectin Antagonist GMI-1271 Show a Favorable Safety, Pharmacokinetic, and Biomarker Profile, Proceedings of the 57$^{th}$ Annual Meeting of the American Society of Hematology, Abstract #1004, Poster Presentation, Dec. 5, 2015, Orlando, FL.
Devata et al., "First in Human Phase 1 Single Dose Escalation Studies of the E-Selectin Antagonist GMI-1271 Show a Favorable Safety, Pharmacokinetic, and Biomarker Profile," Blood, 126(23), Abstract #1004, Dec. 3, 2015.
Devereux, J., et al., "A comprehensive set of sequence analysis programs for the VAX", Nucleic Acids Research 12(1), (1984), 387-395.
Devine, "Rapid Mobilization of CD34+ Cells Following Administration of the CXCR4 Antagonist AMD 3100 to Patients With Multiple Myeloma and Non-Hodgkin's Lymphoma," Journal of Clinical Oncology, 22(6): 1095-1102 (Feb. 23, 2004).
Deweerdt, "Animal models: Towards a myeloma mouse," Nature, 480 (7377): S38-39 (2011).
Diamandis et al., "Reflection on the Discovery of Carcinoembryonic Antigen, Prostate-Specific Antigen, and Cancer Antigens CA125 and CA19-9", Clin Chem, 59(1), Nov. 30, 2012.
Diaz-Ricart et al., "rPSGL-Ig" Drugs of the Future 27(4):346 (2002).
Dimasi et al., "Expression, crystallization and preliminary crystallographic analysis of the extracellular IgV-like domain of the human

(56) References Cited

OTHER PUBLICATIONS natural killer cell inhibitory receptor p75/AIRM1," Acta Crystallographica Section D, Biological Crystallography, 59(Pt 10), 1856-1858, 2003.
Dimasi et al., "Structure of the saccharide-binding domain of the human natural killer cell inhibitory receptor p75/AIR1. Erratum," Acta Crystallographica Section D, Biological Crystallography, 60(Pt 2), Erratta, 401-403, 2004.
Dittmar et al., "Adhesion Molecules and Chemokines: the Navigation System for Circulating Tumor (Stem) Cells to Metastasize in an Organ-Specific Manner," Clin. Exp. Metastasis 25:11-32, 2008.
Doranz et al., "Safe Use of the CSCR4 Inhibitor ALX40-4C in Humans," AIDS Research and Human Retroviruses 17(6):475-486, 2001.
Duijvestijn et al., "High Endothelial Differentiation in Human Lymphoid and Inflammatory Tissues Defined by Monoclonal Antibody HECA-452," Am. J. Path. 130:147-155, 1988.
Dupre et al., "Glycomimetic Selectin Inhibitors: (.alpha.-D-Mannopyranosyloxy)methylbiphenyls," Bioorganic & Medicinal Chemistry Letters 6(5): 569-572, 1996.
Dutta et al "E-selectin inhibition mitigates splenic HSC activation and myelopoiesis in hypercholesterolemic mice with myocardial infarction highlights" Arteriosclerosis, Thrombosis, and Vascular Biology 36(9):1802-08 (2016).
Dykewicz, "Summary of the Guidelines for Preventing Opportunistic Infections among Hematopoietic Stem Cell Transplant Recipients," Clin. Infectious Diseases, 33:139-144, Jul. 15, 2001.
Edgington, "How Sweet It Is: Selectin-Mediating Drugs," Biotechnology 10: 383-389, 1992.
Edwards, "Generally Applicable, Convenient Solid-Phase Synthesis and Receptor Affinities of Octreotide Analogs," J. Med. Chem. 37:3749-3757, 1994.
Egberink et al. "Bicyclams, Selective Antagonists of the Human Chemokine Receptor CXCR4, Potently Inhibit Feline Immunodeficiency Virus Replication," Journal of Virology, 73(8): 6346-6352 (1999).
Eggens et al., "A Role of Carbohydrate-Carbohydrate Interaction in the Process of Specific Cell Recognition During Embryogenesis and Organogenesis: A Preliminary Note," Biochem. Biophys. Res. Commun. 158(3):913-920, 1989.
Eggens et al., "Specific Interaction between Le.sup.X and Le.sup.X Determinants. A Possible Basis for Cell Recognition in Preimplantation Embryos and in Embryonal Carcinoma Cells," J. Biol. Chem. 264(16):9476-9484, 1989.
Egger et al. "Nanomolar E-Selectin Antagonists with Prolonged Half-Lives by a Fragment-Based Approach," JACS, 135(26): 9820-9828 (Jul. 2013).
Embury et al., "The contribution of endothelial cell P-selectin to the microvascular flow of mouse sickle erythrocytes in vivo," Blood 104(10):3378-3385, Nov. 15, 2004.
English Abstract for DE 2434953, Feb. 6, 1975.
English Abstract for JP 9-176047, published Jul. 8, 1997.
English Abstract for JP 2002-520323, published Jul. 9, 2002/.
English Abstract for WO 96/20204, published Jul. 4, 1996.
English Translation of JP 06-0306092, dated Nov. 1, 1994.
English Translation of JP 2004-518704, dated Jun. 24, 2004.
Ernst et al., "Design and Synthesis of E-Selectin Antagonists," Chimia 55:268-274, 2001.
Ernst et al., "From carbohydrate leads to glycomimetic drugs," Nature Reviews 8:661-677, Aug. 2009.
Ernst, "Substrate and donor specificity of glycosyl transferases," Glycoconjugate Journal 16: 161-170, 1999.
Esposito et al., "Exploration of a Potent E-selectin Antagonist (GMI-1271) as a Potential Therapeutic for Treating Breast Cancer Metastasis to the Lung and Bone", AACR Annual Meeting 2014, Poster #4039, Apr. 8, 2014.
Esposito et al., "Exploration of a Potent E-selectin Antagonist (GMI-1271) as a Potential Therapeutic for Treating Breast Cancer Metastasis to the Lung and Bone", Cancer Res, Abstract #4039, Oct. 1, 2014.

Faber et al., "The Many Facets of SDF-1a, CXCR4 Agonists and Antagonists on Hematopoietic Progenitor Cells," J. Biomed. & Biotech. Article ID 26065:1-10, 2007.
Faderl et al., "Clofarabine Plus Cytarabine Compared With Cytarabine Alone in Older Patients With Relapsed or Refractory Acute Myelogenous Leukemia: Results From the CLASSIC I Trial," Journal of Clinical Oncology, 30(20), 2492-2499, 2012.
Feletou, M. et al., "Endothelial dysfunction: a multifaceted disorder," Am. J. Physiol. Heart Circ. Physiol., 291: H985-H1002 (2006).
Fenderson et al., "A Multivalent Lacto-N-Fucopenataose III-Lysyllysine Conjugate Decompacts Preimplantation Mouse Embryos, While the Free Oligosaccharide is Ineffective," J. Exp. Med. 160:1591-1596, 1984.
Fenderson et al., "Coordinate Expression of X and Y Haptens during Murine Embryogenesis," Devel. Biol. 114:12-21, 1986.
Fenderson et al., "The blood group I antigen defined by monoclonal antibody C6 is a marker of early mesoderm during murine embryogenesis," Differentiation 38:124-133, 1988.
Filser, C. et al., "Synthetic glycopeptides from the E-selectin ligand 1 with varied sialyl Lewis(x) structure as cell-adhesion inhibitors of E-selectin," Angewandte Chemie—International Edition, 46(12): 2108-2111 (2007).
Flanner et al., "Comparison of Predicted GMI-1070 Human Intravenous Pharmacokinetics from in silico PBPK and Allometric Scaling Models", AAPS Annual Meeting, Abstract, Nov. 2009.
Frenette, Paul S. et al., "Sulfated Glycans Induce Rapid Hematopoietic Progenitor Cell Mobilization: Evidence for Selectin-Dependent and Independent Mechanisms," Blood, 96:2460-2468, (2000).
Frison, N. et al., "Oligolysine-Based Oligosaccharide Clusters: Selective Recognition and Endocytosis by the Mannose Receptor and Dendritic Cell-Specific Intercellular Adhesion Molecule 3 (ICAM-3)-Grabbing Nonintegrin," The Journal of Biological Chemistry 278(26):23922-23929, Apr. 2003.
Fruehauf, S., et al., "Protection of hematopoietic stem cells from chemotherapy-induced toxicity by multidrug-resistance 1 gene transfer," Recent Results in Cancer Research, 144, Abstract Only), (1998), 1 pQ.
Fukushi et al., "Novel Fucolipids Accumulating in Human Adenocarcinoma," J. Biol. Chem. 259(16):10511-10517 (1984).
Fukushi et al., "Novel Fucolipids Accumulating in Human Adenocarcinoma. II. Selective Isolation of Hybridoma Antibodies That Differentially Recognize Mono-, Di-, and Trifucosylated Type 2 Chain," J. Biol. Chem. 259(7):4681-4685, 1984.
Gabius et al., "Endogenous Tumor Lectins: Overview and Perspectives," Anticancer Res. 6:573-578, 1986.
Gais, H.-J. et al., "Enantioselective and Enantioconvergent Syntheses of Building Blocks for the Total Synthesis of Cyclopentanoid Natural Products," Angewandte Chemie, Int. Ed. Eng. 23(2):142-143, 1984.
Gallatin et al., "A cell-surface molecule involved in organ-specific homing of lymphocyctes," Nature 304:30-34, 1983.
Garber, N. et al., "On the specificity of the D-galactose-binding lectin (PA-I) of Pseudomonas aeruginosa and its strong binding to hydrophobic derivatives of D-galactose and thiogalactose," Biochimica et Biophysica Acta, 1116:331-333 (1992).
Gelbrich, T. et al., "Preparation of 4-benzylsulfanyl[1,2,3,5]dithiadiazol-1-ylium chlorides: potential precursors to meso-ionic 1,2,3,5-dithiadiazolium-4-thiolate," Arkivoc, (vi): 224-223 (2002).
Ghobrial, IM, "Myeloma as a model for the process of metastasis: implications for therapy," 120(1):20-30 (2012).
Gilboa-Gardner, N. et al., "A new mitogenic D-galactosephilic lectin isolated from seeds of the coral-tree Erythrina corallodendron. Comparison with Glycine max (soybean) and Pseudomonas aeruginosa lectins," Canadian Journal of Biochemistry, 59(5):315-320 (1981).
Goodman and Gillman's, "Pharmacological Basis of Therapeutics," 10th edition, p. 54 (2001).
Gooi et al., "Stage-specific embryonic antigen involves alpha 1-3 fucosylated type 2 blood group chains," Nature 292:156-158, 1981.
Gout, et al., "Selectins and selectin ligands in extravasation of cancer cells and organ selectivity of metastasis," Clin. Exp. Metastasis, 25(4): 335-344 (2008).

(56) References Cited

OTHER PUBLICATIONS

Gravina et al., "Abstract 428: Dual E-selectin and CXCR4 inhibition reduces tumor growth and increases the sensitivity to docetaxel in experimental bone metastases of prostate cancer," Cancer Research, 75(15 Supplemental), 428-429, Aug. 2, 2015.
Gravina et al., "Abstract 428: Dual E-selectin and CXCR4 inhibition reduces tumor growth and increases the sensitivity to docetaxel in experimental bone metastases of prostate cancer," Proceedings of the 106$^{th}$ Annual Meeting of the American Association for Cancer Research, Abstract #428, Apr. 18-22, 2015, Philadelphia, PA.
Griciuc et al., "Alzheimer's Disease Risk Gene *CD33* Inhibits Microglial Uptake of Amyloid Beta," Neuron, 78(4), 631-643, May 22, 2013.
Guha et al., "Cod glycopeptide with picomolar affinity to galectin-3 suppresses T-cell apoptosis and prostate cancer metastasis," Proceedings of the National Academy of Science, 110(13), 5052-5057, 2013.
Hakomori, "Aberrant Glycosylation in Cancer Cell Membranes as Focused on Glycolipids: Overview and Perspectives," Cancer Res. 45:2405-2414, 1985.
Hakomori et al., "Novel Fucolipids Accumulating in Human Adenocarcinoma. I. Glycolipids With Di-or Trifucosylated Type 2 Chain," J. Biol. Chem. 259(7):4672-4680, 1984.
Hakomori et al., "The Hapten Structure of a Developmentally Regulated Glycolipid Antigen (SSEA-1) Isolated From Human Erythrocytes and Adenocarcinoma: A Preliminary Note," Biochem. Biophys. Res. Comm. 100(4):1578-1586, 1981.
Halloran et al., "Ley/H: An endothelial-selective cytokine-inducible angiogenic mediator," Journal of Immunology, 164(9): 4868-4877 (May 1, 2000).
Hamamoto et al., "Inhibition of Dextram Sulphat Sodium (DSS)-induced Colitis in Mice by Intracolonically Administered Antibodies Against Adhesion Molecules (Endothelial Leucocyte Adhesion Molecule-1 (ELAM-1) or Intercellular Adhesion Molecule-1 (ICAM-1))", Clinical ExperimentalImmunoloqv, 117, (1999), 462-468.
Handa et al., "Selectin GMP-140 (CD62; PADGEM) Binds to Sialosyl -Le*a* and Sialosyl-Le$^x$, and Sulfated Glycans Modulate this Binding," Biochemical and Biophysical Research Communication 181(3):1223-1230, 1991.
Handschel et al., "Irradiation induces increase of adhesion molecules and accumulation of beta2-integrin-expressing cells in humans" International Journal of Radiation Oncology, Biology, Physics 45(2): 475-481 (1999).
Hansson et al., "Biosynthesis of the Cancer-associated Sialyl-Le. sup.a Antigen," Journal of Biological Chemistry 260(16):9388-9392, 1985.
Harlan, "Introduction-anti-adhesion therapy in sickle cell disease," Blood 95:365-367, 2000.
Hasegawa et al., "Synthesis of deoxy-L-fucose-containing sialyl Lewis X ganglioside analogues," Carbohydrate Research 257: 67-80, 1994.
Hasegawa et al., "Synthesis of sialyl Lewis X ganglioside analogues containing modified L-fucose residues," Carbohydrate Research 274: 165-181, 1995.
Hayashi et al., "Increased Level of Soluble E-Selectin in the Serum from Patients with Idiopathic Pulmonary Fibrosis," Inflammation, 28(1), 1-5, 2004.
Hebbar et al., "E-selectin gene S128R polymorphism is associated with poor prognosis in patients with stage II or III colorectal cancer," European Journal of Cancer, 45, 1871-1876, 2009.
Hebbel, P.R., "Blockade of Adhesion of Sickle Cells to Endothelium by Monoclonal Antibodies," The New England Journal of Medicine 342:1910-1912, Jun. 22, 2000.
Hendrix, C.W. et al., "Pharmacokinetics and Safety of AMD-3100, a Novel Antagonist of the CXCR-4 Chemokine Receptor, in Human Volunteers," Antimicrobial Agents and Chemotherapy 44(6):1667-1673, Jun. 2000.

Hickey et al., "Leukocyte-Endothelial Cell Interactions Are enhanced in Dermal Postcapillary Vemules of MRL/fas$^{lpr}$ (Luplus-Prone) Mice: Roles of P- and E-Selectin," The Journal of Immunology, 168, 4728-4736, 2002.
Hiddemann et al., "Management of Acute Myeloid Leukemia in Elderly Patients," Journal of Clinical Oncology, 17(11), 3569-3576, 1999.
Hilal et al., "Electronic structure of orotic acid I. Geometry, conformational preference and tautomerism:, Journal of Molecular Structure (Theochem)" 685 (2004) 35-42.
Hilgenbrink et al., "Folate receptor-mediated drug targeting: from therapeutics to diagnostics," J. Pharm. Sci., 94(10): 2135-2146 (2005).
Holgate, ST et al., "Epithelium dysfunction in asthma," Current Reviews of Allergy and Clinical Immunology, 120: 1233-1234 (2007).
Holmes et al., "Enzymatic Basis for the Accumulation of Glycolipids with X and Dimeric X Determinants in Human Lung Cancer Cells (NCI-H69)," J. Biol. Chem. 260(12):7619-7627, 1985.
Hong, P. W.-P. et al., "Identification of the Optimal DC-SIGN Binding Site on Human Immunodeficiency Virus Type 1 gp120," Journal of Virology 18(15):8325-8336, Aug. 2007.
Horacek et al., "Multi-analytical evaluation of serum levels of cytokines and adhesion molecules in patients treated for acute myeloid leukemia using biochip array technology," Biomed Pap Med Fac Univ Palacky Olomouc, Czech Repub., 157(4), 277-279, Dec. 2013.
Horiya et al., "Recent strategies targeting HIV glycans in vaccine design," Nature Chemical Biology, 10, 990-999, 2014.
Huang et al., "Postischemic Cerebrovascular E-Selectin Expression Mediates Tissue Injury in Murine Stroke," Stroke, 31, 3047-3053, 2000.
Huse et al., "Generation of a Large Combinatorial Library of the Immunoglobulin Repertoire in Phage Lambda," Science 246:1275-1281, 1989.
Huwe, C. M. et al., "Design, Synthesis and Biological Evaluation of Aryl-substituted Sialyl Lewis X Mimetics Prepared via Cross-metathesis of C-Fucopeptides," Biological & Medicinal Chemistry 7:773-788, 1999.
Hynes, R., "Integrins: A Family of Cell Surface Receptors," Cell 48:549-554, 1987.
Ikeuchi, Yoshihiro et al., "Synthesis and Antitumor Activities of Novel 5-Deazaflavin-Sialic Acid Conjugate Molecules," Bioorg. & Med. Chem. 8:2027-2035, 2000.
International Search Report for PCT/US2017/020091 dated May 8, 2017.
Inwald, D. P. et al., "Platelet and leucocyte activation in childhood sickle cell disease: association with nocturnal hypoxaemia," British Journal of Haematologyl 11:474-481, Nov. 2000.
Ishikawa, F. et al., "Chemotherapy-resistant human AML stem cells home to and engraft within the bone-marrow endosteal region," Nature Biotechnology 25(11):1315-1321, Nov. 2007.
Issekutz, T., "Inhibition of in Vivo Lymphocyte Migration of Inflammation and Homing to Lymphoid Tissues by the TA-2 Monoclonal Antibody. A Likely Role for VLA-4 in Vivo," Journal of Immunology 147:4178-4184, 1991.
Itai, S. et al., "Differentiation-dependent Expression of I and Sialyl I Antigens in the Developing Lung of Human Embryos and in Lung Cancers," Cancer Research 50: 7603-7611, 1990.
Jeffrey et al., "Affinity Chromatography of Carbohydrate-Specific Immunoglobulins: Coupling of Oligosaccharides to Sepharose ," Biochem. Biophys. Res. Commun. 62:608-613, 1975.
Jentsch, K.D. et al., "Inhibition of Human Immunodeficiency Virus Type I Reverse Transcriptase by Suramin-related Compounds," The Journal of General Virology 68(8): 2183-2192, 1987.
Jentsch, TJ et al. "Ion Channels: Function Unravelled by Dysfunction," Nature Cell Biology, 6(11): 1039-1047 (Nov. 2004).
Jiang et al., "CD33 in Alzheimer's Disease," Molecular Neurobiology, 46, 529-535, 2014.
Jubeli et al., "E-selectin as a target for drug delivery and molecular imaging," Journal of controlled Release, 158, 194-206, 2012.

(56) References Cited

OTHER PUBLICATIONS

Juliusson et al., "Age and acute myeloid leukemia: real world data n decision to treat and outcomes from the Swedish Acute Leukemia Registry," Blood, 113, 4170-4187, 2009.
Kaila, N. et al., "β-C-Mannosides as Selectin Inhibitors," Journal of Medicinal Chemistry 45(8): 1563-1566, 2002.
Kaila, N. et al., "Design and synthesis of sialyl Lewis(x) mimics as E- and P-selectin inhibitors," Med Res Rev 22(6):566-601, Nov. 2002.
Kannagi, R. et al. "Carbohydrate-mediated cell adhesion in cancer metastasis and angiogenesis," Cancer Sci., 95(5): 377-384 (2004).
Kannagi et al., "New Globoseries Glycosphingolipids in Human Teratocarcinoma Reactive with the Monoclonal Antibody Directed to a Developmentally Regulated Antigen, Stage-specific Embryonic Antigen 3," J. Biol. Chem. 258(14):8934-8942, 1983.
Kannagi et al., "Stage-specific embryonic antigens (SSEA-3 and -4) are epitopes of a unique globo-series ganglioside isolated from human teratocarcinoma cells," Embo J. 2(12):2355-2361, 1983.
Kansas, G., "Selectins and Their Ligands: Current Concepts and Controversies," Blood, 88(9): 3259-3287 (1996).
Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," Cancer Biochem. Biophys. 11:311-315, 1990.
Katayama, Y., et al., "CD 44 is a physiological E-selectin ligand on neutrophils", J. Exp. Med. 201(8), (2005), 1183-1189.
Katayama, Y. et al., "PSGL-1 Participates in E-Selectin-Mediated Progenitor Homing to Bone Marrow: Evidence for Cooperation Between E-Selectin Ligands and a4 Integrin," Blood, 102:2060-2067, (2003).
Kaul, D.K. et al., "Hypoxia/reoxygenation causes inflammatory response in transgenic sickle mice but not in normal mice," The Journal of Clinical Investigation 106(3):411-420, Aug. 2000.
Khatib, A.-M., et al., "Inhibition of Hepatic Endothelial E-Selectin Expression by C-raf antisense Oligonucleotides Blocks Colorectal Carcinoma Liver Metastasis", Cancer Research 62(19), (2002), 5393-5398.
Kiel, M. J., et al., "SLAM Family Receptors Distinguish Hematopoietic Stem and Progenitor Cells and Reveal Endothelial Niches for Stem Cells" Cell 121 (7) (2006}, 11 09-1121.
Kilgore et al., "Reduction of myocardial infarct size in vivo by carbohydrate-based glycomimetics" Journal of Pharmacology and Experimental Therapeutics, American Society for Pharmacology and Experimental Therapeutics, 284(1):427-435 (1998).
Kim et al., "Inhibition of the CXCR4/CXCL12 Chemokine Pathway Reduces the Development of Murine Pulmonary Metastases," Clin. Exp. Metastasis 25(3):201-211, 2008.
Kitagawa et al., "Characterization of Mucin-Type Oligosaccharides With the Sialyl-Le.sup.a Structure From Human Colorectal Adenocarcinoma Cells," Biochem. Biophys. Res. Commun. 178(3):1429-1436, 1991.
Kitagawa et al., "Immunoaffinity Isolation of a Sialyl-Le$^a$ Oligosaccharide from Human Milk," J. Biochem. 104:591-594, 1988.
Klyosov et al., "Galectins in Disease and Potential Therapeutic Approaches," In Galectins and Disease Implications for Targeted Therapeutics, American Chemical Society, Washington, DC, Chapter 1, pp. 3-43, 2012.
Kneuer et al: "Selectins—potential pharmacological targets?" Drug Discovery Today vol. 11, No. 21-22, pp. 1034-1040, Oct. 2006.
Ko, HL et al. "In Vitro and In Vivo Inhibition of Lectin Mediated Adhesion of Pseudomonas aeruginosa by Receptor Blocking Carbohydrates," Infection, 15(4): 21-24 (1987).
Kobayashi et al., "Cimetidine Inhibits Cancer Cell Adhesion to Endothelial Cells and Prevents Metastasis by Blocking E-selectin Expression," Cancer Research, 60, 3978-3984, 2000.
Koch, Alisa E et al., "Angiogenesis mediated by soluble forms of E-selectin and vascular cell adhesion molecule-1," Nature, 376(6540): 517-519 (1995).
Koenig et al., "Selectin Inhibition: Synthesis and Evaluation of Novel Sialylated, Sulfated and Fucosylated Oligosaccharides, Including the Major Capping Group of Glycam-1", Glycobiology, 7(1):79-93 (1997).
Kogan, T.P. et al., "Novel Synthetic Inhibitors of Selectin-Mediated Cell Adhesion: Synthesis of1,6-Bis[3-(3-carboxymethylphenyl)-r-(2-.alpha.-.sub.D-monnopyranosyloxy)p-henyl]hexane (TBC1269)," J Med. Chem 41:1099-1111, 1998.
Kogan, T.P. et al., "Rational Design and Synthesis of Small Molecule, Non-oligosaccharide Selectin Inhibitors: (.alpha.-D-Mannopyranosyloxy)biphenyl-Substituted Corboxylic Acids," J. Med. Chem. 38: 4976-4984, Dec. 22, 1995.
Kogan, T.P. et al., "Rational Design and Synthesis of Oligosaccharide Mimetics: Selectin Antagonists as Cell Adhesion Inhibitors," Abstracts of Papers, 210.sup.th ACS National Meeting, American Chemical Society, Chicago, IL, Aug. 20-24, 1995, MEDI-18.
Kohler et al., "Continuous cultures of fused cells secreting antibody of predefined specificity," Nature 256:495-497, 1975.
Kohler et al., "Derivation of specific antibody-producing tissue culture and tumor lines by cell fusion," Eur. J. Immunol. 6:511-519, 1976.
Kojima et al., "Specific Interaction between Gangliotriaosylceramide (G.sub.g3) and Sialosyllactosylceramide (G.sub.M3) as a Basis for Specific Cellular Recognition between Lymphoma and Melanoma Cells," J. Biol. Chem. 264(34):20159-20162, 1989.
Kolb et al., "Development of Tool for the Design of Selectin Antagonists," Chem. Eur. J. 3(10):1571-1578, 1997.
Kolb et al., "Recent progress in the glycodrug area," Pure & Applied Chemistry 69(9):1879-1884, 1997.
Komrokji et al., "The Colony-Stimulating Factors: Use to Prevent and Treat Neutropenia and Its Complications," Expert Opin.Biol. Ther., 4:1897-1910, (2004).
Koprowski et al., "Colorectal Carcinoma Antigens Detected by Hybridoma Antibodies," Somatic Cell Genetics 5(6):957-972, 1979.
Kulidjian et al., "Differential role of E-seletin and P-selectin in T lymphocyte migration to cutaneous inflammatory reactions induced by cytokines," International Immunology, 14(7), 751-760, 2002.
Kuuliala et al., "Circulating soluble E-selectin in early rheumatoid arthritis: a prospective five year study," Annals of Rheumatic Diseases, 61, 242-246, 2002.
Kuzuoka, "Antitumor activity of murine monoclonal antibody NCC-ST-421," Chem. Ab. 115:27344v, 1991.
Kwiatskowski et al., "Tautomerism and Electronic Structure of Biological Pyrimidines" Adv Het Chem 1975, pp. 199-335.
Kwong et al., "An Antagonist of the Chemokine Receptor CXCR4 Induces Mitotic Catastrophe in Ovarian Cancer Cells," Mol. Cancer Ther. 8(7): 1893-1905, Jul. 2009.
Kwong, P. D. et al., "Rational Design of Vaccines to Elicit Broadly Neutralizing Antibodies to HIV-1," Cold Spring Harbor Perspectives in Medicine 1-16, 2011.
Kyriakides et al., Surgery, 128(2):327-31, Aug. 2000.
Lamblin et al., "Primary Structure Determination of Five Sialylated Oligosaccharides Derived from Bronchial Mucus Glycoproteins of Patients Suffering from Cystic Fibrosis.," Journal of Biological Chemistry 259(14):9051-9058, 1984.
Lanne, B. et al., "Binding of the galactose-specific Pseudomonas aeruginose lectin, PA-I, to glycosphingolipids and other glycoconjugates," Glycoconjugate Journal, 11:292-298 (1994).
Larsen et al., "PADGEM-Dependent Adhesion of Platelets to Monocytes and Neutrophils is Mediated by a Lineage-Specific Carbohydrate, LNF III (CD15)," Cell 63:467-474, 1990.
Lee et al., "A new method of sequencing linear oligosaccharides on gels using charged, fluorescent coniugates" Carbohydrate Research, vol. 214, 1991, pp. 155-168, XP000226749.
Lemoli et al., "Hematopoietic stem cell mobilization," Haematologica, 93 (3): 321-324 (2008).
Leppla, S H et al., "Anthrax Toxin Fusion Proteins for Intracellular Delivery of Macromolecules," Journal of Applied Microbiology., 87(2): p. 284 (Aug. 1, 1999).
Ley, K. et al., "Selectins in T-cell Recruitment to Non-Lymphoid Tissues and Sites of Inflammation," Nature Reviews, 4: 1-11 (May 2004).

(56) References Cited

OTHER PUBLICATIONS

Ley, K., "The role of selectins in inflammation and disease," Trends in Molecular Medicine, 9(6): 263-268 (Jun. 2003).
Li et al., "Hematopoietic-Derived Galectin-3 Causes Cellular and Systemic Insulin Resistance," Cell, 167, 973-984, 2016.
Li et al., "Increased CSF E-Selectin in Clinical Alzheimer's Disease without Altered CSF $A\beta_{42}$ and Tau," Journal of Alzheimer's Disease, 47, 883-887, 2015.
Li, B., et al., "Delaying Acute Graft-Versus-Host Disease in Mouse Bone Marrow Transplantation by Treating Donor Cells with Antibodies Directed at L-Selectin and a4 Integrin Prior to Infusion," Scand. J, I Immunol 59:464-468, 2004.
Liang et al., "Clinicopathological and prognostic significance of sialyl Lewis X overexpression in patients with cancer: a meta-analysis," Onco Targets and Therapy, 9, 3113-3125, 2016.
Lindenberg et al., "Carbohydrate binding properties of mouse embryos," J. Reprod. Fert. 89:431-439, 1990.
Lipartiti et al., "Monosialoganglioside GM1 Reduces NMDA Neurotoxicity in Neonatal Rat Brain," Experimental Neurology 113:301-305, 1991.
Liu et al., "Altering the Specificity of the Antibody Response to HIV gp120 with a Glycoconjugate Antigen," ACS Chemical Biology, 11, 1702-1709, 2016.
Liu et al., "Broadly Neutralizing Antibody-Guided Carbohydrate-Based HIV Vaccine Design: Challenges and Opportunities," ChemMedChem, 11, 357-362, 2016.
Llmer et al., "Cell surface galectin-3 defines a subset of chemoresistant gastrointestinal tumor-initiating cancer cells with heightened stem cell characteristics," Cell Death and Disease, 7, e2337, 1-9, 2016.
Loetscher et al., "N-terminal Peptides of Stromal Cell-derived Factor-1 with CXC Chemokine Receptor 4 Agonist and Antagonist Activities," J. Biol. Chem. 273(35):22279-22283, 1998.
Lowe et al., "A transfected human fucosyltransferase cDNA determines biosynthesis of oligosaccharide ligand(s) for endothelial-leukocyte adhesion molecule I," Biochem. Soc. Trans. 19(3):649-653, 1991.
Lowe et al., "ELAM-1-Dependent Cell Adhesion to Vascular Endothelium Determined by a Transfected Human Fucosyltransferase cDNA," Cell 63:475-484, 1990.
Luallen, R. J. et al., "A Yeast Glycoprotein Shows High-Affinity Binding to the Broadly Neutralizing Human Immunodeficiency Virus Antibody 2G12 and Inhibits gp120 interactions with 2G12 and DC-SIGN," Journal of Virology 83(1):4861-4870, May 2009.
Macher et al., "A Novel Carbohydrate, Differentiation Antigen on Fucogangliosides of Human Myeloid Cells Recognized by Monoclonal Antibody VIM-2," Journal of Biological Chemistry 263(21):10186-10191, 1988.
Magnani et al., "A Monoclonal Antibody-defined Antigen Associated with Gastrointestinal Cancer Is a Ganglioside Containing Sialylated Lacto-N-fucopentaose II," Journal of Biological Chemistry 257(23):14365-14369, 1982.
Magnani et al., "Identification of the Gastrointestinal and Pancreatic Cancer-associated Antigen Detected by Monoclonal Antibody 19-9 in the Sera of Patients as a Mucin," Cancer Res. 43:5489-5492, 1983.
Magnani et al., "Glycomimetic Drugs—A New Source of Therapeutic Opportunities," Discovery Medicine, 8(43), 247-252, 2009.
Magnani et al., "Pan-selectin Antagonist GMI-1070 affects Biomarkers of Adhesion, Activation and the Coagulation Cascade in Sickle Cell Adults at Steady State", Blood, 120, Abstract #87, Nov. 2012.
Magnani, "The Discovery, Biology, and Drug Development of Sialyl Le$^a$ and Sialyl Le$^x$", Archives of Biochemistry and Biophysics, 426:122-131, May 8, 2004.
Magnani, J., "Carbohydrate Sequences Detected by Murine Monoclonal Antibodies," Chemistry and Physics of Lipids 42:65-74, 1986.
Magnani, J., "Potent Glycomimetic Inhibitors of the Adhesion Molecule, PA-IIL, for the Bacterial Pathogen, Pseudomonas auroginosa," Glycobiology 13(11): 854, Abstract No. 104, Oct. 2003.

Maly, P., et al., "The a(1,3)Fucosyltransferase Fuc-TVII Controls Leukocyte Trafficking through an Essential Role in L-, E-, and P-selection Ligand Biosynthesis", Cell. 86(4), It 1996), 643-653.
Mann, AP et al., "Identification of Thioaptamer Ligand against E-Selectin: Potential Application for Inflamed Vasculature Targeting," PLoS ONE, 5(9): 1-11 (Sep. 2010).
Matsuda, Masao et al., "Heterobifunctional Ligands: Practical Chemoenzymatic Synthesis of a Cell Adhesive Glycopeptide That Interacts With Both Selectins and Integrins," J. Med. Chem. 44:715-724, 2001.
Matsui, N. M. et al., "Heparin inhibits the flow adhesion of sickle red blood cells to Pselectin," Blood 100(10):3790-3796, Nov. 15, 2002.
Matsui, N. M. et al., "The Novel Adhesion of Erythrocytes to P-Selectin in Sickle Cell Disease," Blood 96(11) Pt. 1:600a, Abstract #2575, Nov. 16, 2000.
Matsui, N. M.et al., "P-selectin mediates the adhesion of sickle erythrocytes to the endothelium," Blood 98(6):1955-1962, Sep. 15, 2001.
Mauch, P., et al., "Hematopoietic Stem Cell Compartment: Acute and Late Effects of Radiation Therapy and Chemotherapy", Int. J. Radiation Oncology Biol. Phys .. 31(5), 1995), 1319-1339.
McCavit et al., "An Analysis of the Pediatric Sub-Group From the Phase 2 Study of GMI-1070—A Novel Agent for the Vaso-Occlusive Crisis of Sickle Cell Anemia", Blood, 122(21):2206, Nov. 15, 2013.
McCavit et al., "An Analysis of the Pediatric Sub-Group From the Phase 2 Study of GMI-1070—A Novel Agent for the Vaso-Occlusive Crisis of Sickle Cell Anemia", ASH Annual Meeting 2013, Poster #56448, Dec. 8, 2013.
McEver et al., "Leukocyte trafficking mediated by selectin-carbohydrate interactions," J. Biol. Chem., 270 (19): 11025-11028 (1995).
McKenzie et al., "Low rhodamine 123 retention identifies long-term human hematopoietic stem cells with the Lin—CD34+CD38-population", Blood. 109, (2007), 543-545.
McLean et al., "Effects of a small molecule inhibitor of ICAM-1 and E-selectin expression on colonic inflammatory hyperalgesia and colitis" Digestive Disease 2003, Orlando FL, May 2003, abstract.
Menendez et al., "A Peptide Inhibitor of HIV-1 Neutralizing Antibody 2G12 is not a Structural Mimic of the Natural Carbohydrate Epitope on gp120," The FASEB Journal 22:1380-1382, May 2008.
Mimeault, et al., "Stem cells: a revolution in therapeutics-recent advances in stem cell biology and their therapeutic applications in regenerative medicine and cancer therapies," Clin. Pharmacol. Therapeutics, 82(3): 252-264 (2007).
Mitsiades, et al., "Preclinleal studies in support of defibrotide for the treatment of multiple myeloma and other neoplasias," Clin. Cancer Res., 15 (4): 1210-1221 (2009).
Moore et al., "Evolution of an HIV Glycan-Dependent Broadly Neutralizing Antibody Epitope Through Immune Escape," Nature Medicine doi:10.1038/nm.2985 pp. 1-6, Oct. 2012.
Moore, "Waking Up HSCs: A new Role for E-Selectin," Nat. Med., 18:16131614, (2012).
Mosley et al., "Recent Patents Regarding the Discovery of Small Molecule CXCR4 Antagonists," Expert Opin. Ther. Patents 19(1):23-38, 2009.
Mulligan et al., "Role of Endothelial-Leukocyte Adhesion Molecule 1 (ELAM-1) in Neutrophil-mediated Lung Injury in Rats," J Clin Invest.,88(4):1396-406, Oct. 1991.
Mulligan et al., "Selection for animal cells that express the *Escherichia coli* gene coding for xanthine-gunine phosphoribosyltransferase," Proc. Natl. Acad. Sci. USA 78:2072-2076, 1981.
Myers et al., "E-Selectin Inhibitor GMI-1271 Works in Combination with Low-Molecular Weight Heparin to Decrease Venous Thrombosis and Bleeding Risk in a Mouse Model", Blood, 124(21):593, Dec. 6, 2014.
Myers et al., "Novel E-Selectin Antagonist GMI-1271 Decreases Venous Thrombosis without Increased Bleeding Potential in a Mouse Model", ASH Annual Meeting 2012, Poster #53444, Dec. 10, 2012.

(56) References Cited

OTHER PUBLICATIONS

Myers et al., "Pan-Selectin Antagonist, GMI-1070 Decreases Venous Thrombosis in a Mouse Model", Blood, 118, Abstract #3273, Nov. 2011.
Myers Jr. et al., "E-Selectin Inhibitor GMI-1271 Works in Combination with Low-Molecular Weight Heparin to Decrease Venous Thrombosis and Bleeding Risk in a Mouse Model," Proceedings of the 56th Annual Meeting of the American Society of Hematology, Abstract #593 Oral Presentation on Dec. 8, 2014, San Francisco, CA.
Myers Jr. et al., "Novel E-Selectin Antagonist GMI-1271 Decreases Venous Thrombosis without Increased Bleeding Potential in a Mouse Model," Blood, 120(21), Abstract #3422, Nov. 16, 2012.
Myers Jr. et al., "Novel E-Selectin Antagonist GMI-1271 Decreases Venous Thrombosis without Increased Bleeding Potential in a Mouse Model," Proceedings of the 54th Annual Meeting of the American Society of Hematology, Abstract #3422 Poster Presentation on Dec. 10, 2012, Atlanta, GA.
Nagel, R. L., "A Knockout of a Transgenic Mouse-Animal Models of Sickle Cell Anemia," The New England Journal of Medicine 339:194-195, Jul. 16, 1998.
Narita, T. et al., "Corticosteroids and medroxyprogesterone acetate inhibit the induction of breast cancer cells," Anticancer Research, 15(6B): 2523-2527 (1995)—ABSTRACT.
Narumi, Tetsuo et al., "Synthesis and Biological Evaluation of Selective CXCR4 Antagonists Containing Alkene Dipeptide Isosteres," Organic & Biomolecular Chemistry, 8(3): 616-621(Feb. 7, 2010).
Natarajan, M.M. et al., "Adhesion of sickle red blood cells and damage to interleukinlbeta stimulated endothelial cells underflow in vitro," Blood 87:4845-4852, 1996.
Natoni et al., "E-Selectin Ligand Expression Increases with Progression of Myeloma and Induces Drug Resistance in a Murine Transplant Model, Which Is Overcome by the Glycomimetic E-Selectin Antagonist, GMI-1271," Blood, 126(23), Abstract#1805, Dec. 3, 2015.
Natoni et al., "E-Selectin Ligand Expression Increases with Progression of Myeloma and Induces Drug Resistance in a Murine Transplant Model, Which Is Overcome By the Glycomimetic E-Selectin Antagonist, GMI-1271," Proceedings of the 57th Annual Meeting of the American Society of Hematology, Abstract #1805 Poster Presentation on Dec. 5, 2015 in Orlando, FL.
Natoni et al., "Multiple Myeloma Cells Express Functional E-Selectin Ligands Which Can be Inhibited Both in-Vitro and in-Vivo Leading to Prolongation of Survival in a Murine Transplant Model", Blood, 124(21):4718, Dec. 6, 2014.
Natoni et al., Multiple Myeloma Cells Express Functional E-Selectin Ligands Which Can be Inhibited Both in vitro and in vivo Leading to Prolongation of Survival in a Murine Transplant Model, Proceedings of the 56th Annual Meeting of the American Society of Hematology, Abstract #4718 Poster Presentation on Dec. 8, 2014 in San Francisco, CA.
Newlaczyl et al., "Galectin-3—A jack-of-all-trades in cancer," Cancer Letters, 313, 123-128, 2011.
Nguyen, M et al., "Novel synthetic analogs 1-29 of sialyl Lewis X can inhibit angiogenesis in vitro and in vivo," Biochemical and Biophysical Research Communications, 228(3): 716-723 (Nov. 21, 1996).
Nicolaou et al., "Total Synthesis of the Tumor-Associated $Le^x$ Family of Glycosphingolipids," J. Amer. Chem. Soc. 112:3693-3695, 1990.
Noguchi, M. et al. "A minor E-selectin ligand, CD65, is critical for extravascular infiltration of acute myeloid leukemia cells," Leukemia Research, 25: 847-853 (2001).
Norman et al., "Sialyl Lewisx(sLex) and an sLex Mimetic, CGP69669A, Disrupt E-Selectin-Dependent Leukocyte Rolling In Vivo," Blood, 91(2):475-483 (Jan. 15, 1998).
Nudelman et al., "Novel Fucolipids of Human Adenocarcinoma: Disialosyl Lea Antigen (III.sup.4FucIII.sup.6NeuAcIV.sup.3NeuAcLc. sub.4) of Human Colonic Adenocarcinoma and the Monoclonal Antibody (FH7) Defining This Structure," J. Biol. Chem. 261:5487-5495,1986.
Nutku, E. et al., "Ligation of Siglec-8: a selective mechanism for induction of human eosinophil apoptosis," Blood, 101(12): 5014-5020 (2003).
Oancea et al., "Alleviation of Acute Drug-Induced Liver Injury Following Acetaminophen Overdose by Therapeutic Blockade of E-Selectin in Preclinical Mouse Model," Gastroenterology, 150(4), Supplement 1, S1029, Abstract #358, (no oral presentation available) New Orleans, LA, Apr. 2016.
Obermajer, N. et al., "Design, synthesis and activity evaluation of mannose-based DC-SIGN antagonists," Molecular Diversity 15:347-360, May 2011.
Orhlein, R., "Carbohydrates and Derivatives as Potential Drug Candidates with Emphasis on the Selectin and Linear-B Area," Mini Reviews in Medicinal Chemistry 1: 349-361, 2001.
Oxford Textbook of Oncology, vol. 1, published 1995 by Oxford University Press, pp. 447-453.
Palcic et al., "A Bisubstrate Analog Inhibitor for .alpha.(1.fwdarw.2)-Fucosyltransferase," J. Biol. Chem. 264:17174-17181, 1989.
Palcic et al., "Enzymic Synthesis of Oligosaccharides Terminating in the Tumor-Associated Sialyl-Lewis-a Determinant," Carbohydr. Res. 190:1-11, 1989.
Palcic et al., "Regulation of N-Acetylglucosaminyltransferase V Activity. Kinetic Comparisons of Parental, Rous Sarcoma Virus-Transformed BHK, and .sub.L-Phytohemagglutinin-Resistant BHK Cells Using Synthetic Substrates and an Inhibitory Substrate Analog," J. Biol. Chem. 265:6759-6769, 1990.
Palma-Vargas, J.M. et al., "Small-Molecule Selectin Inhibitor Protects Against Liver Inflammatory Response After Ischemia and Reperfusion," J. Am. Coll. Surg. 185: 365-372, 1997.
Pamphilon et al., "Stem Cell Donation—What advice can be given to the donor?," Br. J. Haematol. 147(1):71-76, Oct. 2009, Author manuscript available at NIH Public access Aug. 1, 2012.
Patton, J. T. et al., "GMI-1070: a Small Glycomimetic, Pan-selectin Antagonist that Improves Blood Flow and Inhibits Blood Cell Adhesion in Sickle Mice," Abstract ID:ABSTY-5APYL-CA6TP-V2ET6, Sep. 2, 2005.
Payre, et al., "Chemoenzymatische Synthese eines zweifach modifizierten Pentasaccharids als Substrat fur einen alpha-Amylase-Assay durch Fluoreszenz-loschung" Angew. Chem., vol. 107, No. 11, 1995, pp. 1361-1364.
Payre, N. et al., "Chemoenzymatic Synthesis of a Modified Pentasaccharide as a Specific Substrate for a Sensitive Assay of a-Amylase by Fluorescence Quenching," Angew. Chem. Int. Ed. Engl. 34(11): 1239-1241 (1995).
Peacock et al., "Emergency Department Use of Galectin-3," Critical Pathways in Cardiology, 13(2), 73-77, 2014.
Pejchal R. et al., "A Potent and Broad Neutralizing Antibody Recognizes and Penetrates the HIV Glycan Shield," Science 334:1097-1103, Nov. 2011.
Pelus, "Peripheral blood stem cell mobilization: new regimens, new cells, where do we stand," Curr. Opin. Hematol., 15(4): 285-292 (2008).
Pentelute, Brad et al., "A Semisynthesis Platform for Investigating Structure-Function Relationships in the N-Terminal Domain of the Anthrax Lethal Factor," ACS Chemical Biology. 5(4): 359-364 (Apr. 2010).
Pentelute, Brad L. et al., "Chemica 1 1-16 dissection of protein translocation through the anthrax toxin pore," Angewandte Chemie, 50(10): 2294-2296 (Mar. 1, 2011).
Perret, S. et al., "Structural basis for the interaction between human milk oligosaccharides and the bacterial lectin PA-IIL of Pseudomonas aeruginosa," Biochem. J. 389: 325-332, 2005.
Pezeshkian et al., "Leukemia Mediated Endothelial Cell Activation Modulates Leukemia Cell Susceptibility to Chemotherapy through a Positive Feedback Loop Mechanism," PLOS One, 8(4), e60823, 2013.
Phillips et al., "ELAM-1 Mediates Cell Adhesion by Recognition of a Carbohydrate Ligand, Sialyl-Le.sup.x," Science 250:1130-1132, 1990.

(56) References Cited

OTHER PUBLICATIONS

Picker er al., "The Neutrophil Selectin LECAM-1 Presents Carbohydrate Ligands to the Vascular Selectins ELAM-1 and GMP-140," Cell 66:921-933, 1991.
Plasterk, R. H. A., et al., "The silence of the genes", Current Opinion in Genetics and Develooment 10 (2000), 562-567.
Price et al., "Breast Cancer Cells Metastasize to Bone through E-Selectin Positive Vascular Gateways", AACR Annual Meeting 2014, Poster #4831, Apr. 9, 2014.
Price et al., "Breast cancer cells metastasize to bone through E-selectin + vascular gateways," Cancer Research, 74(19 Supplement), 4831, Sep. 20, 2014.
Price et al., "Breast Cancer Cells Metastasize to Bone through E-Selectin Positive Vascular Gateways," Proceedings of the 105th Annual Meeting of the AACR, 4831, Apr. 5-9, 2014, San Diego, CA.
Price et al., "Metastatic breast cancer cell communication within a pro-dormancy bone marrow niche," Cancer Research, 75(15 Supplement), Abstract #3212, Aug. 2015.
Price et al., "Metastatic Breast Cancer Cell Communication Within a Pro-Dormancy Bone Marrow Niche," Proceedings of the 106th Annual Meeting of the American Association for Cancer Research, Abstract #3212, Apr. 18-22, 2015, Philadelphia, PA.
Prokazova et al., "Sialylated lactosylceramides. Possible inducers of non-specific immunosuppression and atherosclerotic lesions," European Journal of Biochemistry 172:1-6, 1988.
Purton et al., "Limiting Factors in Murine Hematopoietic Stem Cell Assays," Cell Stem Cell 1: 263-270, Sep. 2007.
Rapoport et al., "Ganglioside Binding Pattern of CD33-Related Siglecs," Bioorganic and Medicinal Chemistry Letters, 13(4), 675-678, Feb. 2003.
Rapoport, E. et al., "Probing Sialic Acid Binding Ig-Like Lectins (Siglecs) with Sulfated Oligosaccharides," Biochemistry (Moscow), 71(5): 496-504 (2006).
Rauvala et al., "Studies on Cell Adhesion and Recognition. I. Extent and Specificity of Cell Adhesion Triggered by Carbohydrate-reactive Proteins (Glycosidases and Lectins) and by Fibronectin," J. Cell Biol. 88:127-137, 1981.
Ravandi et al., "Characteristics and outcome of patients with acute myeloid leukemia refractory to 1 cycle of high-dose cytarabine-based induction chemotherapy," Blood 116(26), 5818-5823, 2010.
Reina et al., "1,2-Mannobioside Mimic: Synthesis, DC-SIGN Interaction by NMR and Docking, and Antiviral Activity," ChemMedChem 2:1030-1036, 2007.
Rice et al., "An Inducible Endothelial Cell Surface Glycoprotein Mediates Melanoma Adhesion," Science 246:1303-1306, 1989.
Richert et al., "Inhibition of CXCR4 by CTCE-9908 Inhibits Breast Cancer Metastasis to Lung and Bone," Oncology Reports 21:761-767, 2009.
Roberge, J. Y., et al., "A Strategy for a Convergent Synthesis of N-Linked Glycopeptides on a Solid Support", Science 269(5221), (1995), 202-204.
Röllig et al., "Long-Term Prognosis of Acute Myeloid Leukemia According to the New Genetic Risk Classification of the European LeukemiaNet Recommendations: Evaluation of the Proposed Reporting System," Journal of Clinical Oncology, 29(20), 2758-2765, 2011.
Rood et al., "E-Selectin and Very Late Activation Antigen-r Mediate Adhesion of Hematopoietic Progenitor Cells to Bone Marrow Endothelium," Ann Hematol, 79:477-484, (2000).
Ruoslahti et al., "New Perspectives in Cell Adhesion: RGD and Integrins," Science 238:491-497, 1987.
Sackstein, "The Biology of CD44 and HCELL in Hematopoiesis: The 'Step 2-Bypass Pathway' and Other Emerging Perspectives", Current Opinion in Hematology, 18(4):239-248 (2011).
Sakurai et al., "Selection of a Monoclonal Antibody Reactive with a High-Molecular-Weight Glycoprotein Circulating in the Body Fluid of Gastrointestinal Cancer Patients," Cancer Research 48:4053-4058, 1988.

Salameh et al., "1H-1,2,3-Triazol-1-yl thiodigalactoside derivatives as high affinity galectin-3 inhibitors," Bioorganic & Medicinal Chemistry, 18, 5367-5378, 2010.
Sanz et al., "Roflumilast inhibits leukocyte-endothelial cell interactions, expression of adhesion molecules and microvascular permeability", British Journal of Pharmacology. 152(4), (2007), 481-492.
Sastry et al., "Cloning of the immunological repertoire in *Escherichia coli* for generation of monoclonal catalytic antibodies: Construction of a heavy chain variable region-specific cDNA library," Proc. Natl. Acad. Sci. USA 86:5728-5732, 1989.
Scanlan et al., "Exploiting the Defensive Sugars of HIV-1 for Drug and Vaccine Design," Nature 446:1038-1045, Apr. 2007.
Scanlan et al., "The Broadly Neutralizing Anti-Human Immunodeficiency Virus Type 1 Antibody 2G12 Recognizes a Cluster of a1-2 mannose Residues on the Outer Face of gp120," Journal of Virology 76:7306-7321, Jul. 2002.
Scharfman et al., "Pseudomonas aeruginosa binds to neoglycoconjugates bearing mucin carbohydrate determinants and predominantly to sialyl-Lewis x conjugates," Glycobiology 9(8): 757-764, 1999.
Scharfman et al., "Recognition of Lewis x Derivatives Present on Mucins by Flagellar Components of Pseudomonas aeruginosa," Infection and Immunity 69(9): 5243-5248, Sep. 2001.
Schief et al., "Challenges for Structure-Based HIV Vaccine Design," Current Opinion in HIV and AIDS 4:431-440, 2009.
Schwizer et al. "Pre-organization of the Core Structure of E-Selectin Antagonist," Chemistry—A European Journal, 18(5): 1342-1351 (Jan. 2012).
Shamay et al., "E-selectin binding peptide-polymer-drug conjugates and their selective cytotoxicity against vascular endothelial cells," Biomaterials, 30, 6460-6468, 2009.
Shan, M. et al., "HIV-1 gp120 Mannoses Induce Immunosuppressive Responses from Dendritic Cells," PLoS Pathogens 3(11):e169 1637-1650, Nov. 2007.
Sheen-Chen et al., "Serum levels of soluble E-selectin in women with breast cancer," British Journal of Surgery, 91, 1578-1581, 2004.
Shitara et al., "Application of Anti-Sialyl Le.sup.a Monoclonal antibody, KM231, for Immunotherapy of Cancer," Anticancer Res. 11:2003-2014, 1991.
Simanek et al. "Selectin-carbohydrate interactions: from natural ligands to designed mimics", Chemical Reviews vol. 98, No. 2, pp. 833-862, Jan. 1998.
Simon et al, "Effects of Selectin Antagonist GMI-1070 on the Activation State of Leukocytes in Sickle Cell Patients not in Crisis" ASH Annual Meeting 2010, Poster #32407, Dec. 6, 2010.
Simon et al., "Inhibition of E-Selectin Inflammatory Function by the Glycomimetic GMI-1070" Blood, 118, Abstract #851, Nov. 2011.
Simon et al., "Mightier than the sickle cell (editorial)", Blood, 116(10), 1633, Sep. 9, 2010.
Singh et al., "Evaluation of a CXCR4 Antagonist in a Xenograft Mouse Model of Inflammatory Breast Cancer," Clin. Exp. Metastasis 27:233-240, Mar. 2010.
Sipkins et al., "In Vivo Imaging of Specialized Bone Marrow Endothelial Microdomains for Tumor Engraftment," Nature Pub. Group GB 435 (7044):969-973, Jun. 2005.
Siuzdak et al., "Examination of the Sialyl Lewis X—Calcium Complex by Electrospray Mass Spectrometry," Bioorganic & Medicinal Chemistry Letters 4(24): 2863-2866, 1994.
Solovey et al., "Circulating Activated Endothelial Cells in Sickle Cell Anemia," The New England Journal of Medicine 337:1584-1590, Nov. 27, 1997.
Solovey et al. "Modulation of endothelial cell activation in sickle cell disease: a pilot study," Blood, 97(7): 1937-1941 (Apr. 2001).
Sprengard et al., "Synthesis and Biological Activity of Novel Sialyl-Lewis.sup.X Conjugates," Bioorganic & Medicinal Chemistry Letters 6(5): 509-514, 1996.
Stanley et al., "The LEC11 Chinese Hamster Ovary Mutant Synthesizes N-Linked Carbohydrates Containing Sialylated, Fucosylated Lactosamine Units. Analysis by One- and Two-Dimensional H NMR Spectroscopy," J. Biol. Chem. 263(23):11374-11381, 1988.
Steele et al., "#4503 A Small Molecule Glycomimetic Antagonist of E-selectin (GMI-1271) Prevents Pancreatic Tumor Metastasis and

(56) References Cited

OTHER PUBLICATIONS

Offers Improved Efficacy of Chemotherapy," Proceedings of the 105th Annual Meeting of the American Association for Cancer Research, Abstract #4503, Apr. 5-9, 2014, San Diego, CA.

Steele et al., "425 A small molecule glycomimetic antagonist of E-selectin and CXCR4 (GMI-1359) prevents pancreatic tumor metastasis and offers improved chemotherapy" Cancer Research, Aug. 2015.

Steele et al., "425 A Small Molecule Glycomimetic Antagonist of E-selectin and CXCR4 (GMI-1359) Prevents Pancreatic Tumor Metastasis and Offers Improved Chemotherapy," Proceedings of the 106th Annual Meeting of the American Association for Cancer Research, Abstract #425, Apr. 18-22, 2015, Philadelphia, PA.

Steele et al., "A Small Molecule Glycomimetic Antagonist of E-selectin (GMI-1271) Prevents Pancreatic Tumor Metastasis and Offers Improved Efficacy of Chemotherapy", AACR Annual Meeting 2014, Poster #4503, Apr. 8, 2014.

Steele et al., "A Small Molecule Glycomimetic Antagonist of E-selectin (GMI-1271) Prevents Pancreatic Tumor Metastasis and Offers Improved Efficacy of Chemotherapy", Cancer Res, 74:Abstract 4503, Oct. 1, 2014.

Steele et al., "A small molecule glycomimetic antagonist of E-selectin and CXCR4 (GMI-1359) prevents pancreatic tumor metastasis and improves chemotherapy," Cancer Research, 75(15 Supplement), 425-426, Aug. 2, 2015.

Steele et al., "A small molecule glycomimetic antagonist of E-selectin and CXCR4 (GMI-1359) delays pancreatic tumor metastasis and significantly alters the pancreatic tumor microenvironment," Proceedings of the 107th Annual Meeting of the American Association for Cancer Research, Abstract #902, Apr. 16-20, 2016, New Orleans, LA.

Steele et al., "Abstract 4503: A small molecule glycomimetic antagonist of E-selectin (GMI-1271) prevents pancreatic tumor metastasis and offers a novel treatment for improved efficacy of chemotherapy," Cancer Research, 74(19 Supplement), Abstract #4503, Oct. 2014.

Stephens et al.,"The construction of highly efficient and versatile set of mammalian expression vectors," Nucleic Acids Research. 17:7110, 1989.

Stevenson et al., "Differential metastasis inhibition by clinically relevant levels of heparins," Clin. Cancer Res. 11(19): 7003-7011 (2005).

Streeter et al., "Immunohistologic and Functional Characterization of a Vascular Addressin Involved in Lymphocyte Homing into Peripheral Lymph Nodes," Journal of Cell Biology 107: 1853-1862, 1988.

Stroud et al. ,"Extended Type 1 Chain Glycosphingolipids: Dimeric Le.sup.a (III.sup.4V.sup.4Fuc.sub.2Lc.sub.6) as Human Tumor-associated Antigen," J. Biol. Chem. 266(13):8439-8446, 1991.

Styles et al., GMI-1070, a Pan-Selectin Inhibitor: Safety and PK in a Phase 1/2 Study in Adults with Sickle Cell Disease, ASH Annual Meeting 2010, Poster #31824, Dec. 4, 2010.

Sudhoff et al., "Cutting Edge Communication: Circulating Endothelial Adhesion Molecules (sE-Selectin, sVCAM-1 and SICAM-1) During rHuG-CSF-Stimulated Stem Cell Mobilization," Jour. Hematother. & Stem Cell Res., 11:147-151 (2002).

Supplementary European Search Report in EP 03739223 dated Jan. 16, 2009.

Suzuma et al., "Contribution of E-Selectin to Cellular Infiltration during Endotoxin-Induced Uveitis," Invest. Ophthalmol. Vis. Sci., 39: 1620-1630 (1998).

Svenson et al., "Coupling of Acid Labile *Salmonella* Specific Oligosaccharides to Macromolecular Carriers," J. Immunol. Meth. 25:323-335, 1979.

Symon et al., "Selectins and their Counter receptors: a bitter sweet attraction," Thorax, 51:1155-1157 (1996).

Tabarani et al., "Mannose Hyperbranched Dendritic Polymers Interact with Clustered Organization of DC-SGIN and Inhibit gp120 Binding," FEBS Letters 580:2402-2408, Mar. 2006.

Takada et al., "Adhesion of Human Cancer Cells to Vascular Endothelium Mediated by a Carbohydrate Antigen, Sialyl Lewis $A^1$," Biochem. Biophys. Res. Commun. 179(2):713-719, 1991.

Takahashi et al., "Design and Synthesis of a Water-Soluble Taxol Analogue : Taxol-Sialyl Conjugate," Bioorg. & Med. Chem. Letters 8:113-116, 1998.

Takeichi, "Cadherins: a molecular family essential for selective cell-cell adhesion and animal morphogenesis," Trends Genet. 3(8):213-217, 1987.

Tamamura, et al., "Identification of a New Class of Low Molecular Weight Antagonists against the Chemokine Receptor CXCR4 Having the Dipicolylamine-Zinc(II) Complex Structure" J. Med. Chem., 49: 3412-3415 (2006).

Tanaka et al., "Azamacrocyclic Metal Complexes as CXCR4 Antagonists," ChemMedChem, 6: 834-839 (2011).

Taniguchi et al., "Serum Levels of Galectin-3: Possible Association with Fibrosis, Aberrant Angiogenesis, and Immune Activation in Patients with Systemic Sclerosis," The Journal of Rheumatology, 39(3), 539-544, Mar. 2012.

Tedder et al., "The selectins: vascular adhesion molecules," FASEB J, 9(10): 866-73 (1995).

Tejler et al., "Fragment-based development of triazole-substituted O-galactosyl aldoximes with fragment-induced affinity and selectivity for galectin-3," Organic & Biomolecular Chemistry, 19(7), 3982-3992, 2009.

Tejler et al., "Synthesis of galactose-mimicking 1H-(1,2,3-triazol-I-yl)-mannosides as selective galectin-3 and 9N inhibitors," Carbohydrate Research, 342(12-13), 1869-1875, 2007.

Telen et al., "GMI 1070: Reduction in Time to Resolution of Vaso-Occlusive Crisis and Decreased Opioid Use in a Prospective, Randomized, Multi-Center Double Blind, Adaptive Phase 2 Study in Sickle Cell Disease" Blood, 122(21):776, Nov. 15, 2013.

Telen et al., "Randomized phase 2 study of GMI-1070 in SCD: reduction in time to resolution of vaso-occlusive events and decreased opioid use", Blood, 125(17):2656-2664, Apr. 23, 2015.

The Merck Manual of Diagnosis and Therapy, Seventeenth Edition, published 1999 by Merck Research Laboratories, pp. 397, 398, 948,949, 1916, 1979-1981.

Thoma G. et al., "A readily Available, Highly Potent E-Selectin Antagonist," Angew. Chem. Int. Ed. 40(19): 3644-3647, 2001.

Thoma, G et al., "Nanomolar E-selectin inhibitors: 700-fold potentiation of affinity by multivalent ligand presentation," Journal of the American Chemical Society, 123(41): 10113-10114 (Oct. 17, 2001).

Thoma, G. et al., "Preorganization of the Bioactive Conformation of Sialyl Lewis$^x$ Analogues Correlates with Their Affinity to E-Selectin," Angew. Chem. Int. Ed. 40(10): 1941-1945, 2001.

Thoma, G. et al., "Synthesis and biological evaluation of a potent E-selectin antagonist," J. Med. Chem. 42 (23): 4909-4913, Nov. 18, 1999.

Thoma, G. et al., "Synthesis and Biological Evaluation of a Sialyl Lewis X Mimic with Significantly Improved E-selectin Inhibition," Bioorganic & Medicinal Chemistry Letters 11: 923-925, 2001.

Tilton, R.G., "Endotoxin-Induced Leukocyte Accumulation in Aqueous Fluid of Rats is Decreased by a Small Molecule Selectin," Investigative Opthalmology & Visual Science 37(3): S918, Abstract No. 4227, Feb. 15, 1996.

Titz et al., "Is adamantine a suitable substituent to pre-organize the acid orientation in E-selectin antagonists?", Bioorganic & Medicinal Chemistry, 16 (2008), 1046-1056.

Titz et al., "Mimetics of Sialyl Lewis$^x$: The Pre-Organization of the Carboxylic Acid is Essential for Binding to Selectins", Chimia, 61:194-197, 2007.

Titz, A. et al., "Probing the carbohydrate recognition domain of E-selectin: The importance of the acid orientation in sLex mimetics," Bioorg. Med. Chem., 18(1): 19-27 (2010).

Todderund et al., "BMS-190394, a Selectin Inhbitor, Prevents Rat Cutaneous Inflammatory Reactions," J Pharmacal Exp Ther., 282(3):1298-304, Sep. 1997.

Toepfer et al., "Synthesis of Novel Mimetics of the Sialyl Lewis X Determinant," Tetrahedron Letters, vol. 36, No. 50, pp. 9161-9164, 1995.

(56) References Cited

OTHER PUBLICATIONS

Togel et al., "Administered mesenchymal stem cells protect against ischemic acute renal failure through differentiation-independent mechanisms," Am. J. Physical Renal Physiol., 289:F31-42, Jul. 2005.
Totani, K. et al., "Chemoenzymatic synthesis and application of glycopolymers containing multivalent sialyloligosaccharides with a poly(L-glutamic acid) backbone for inhibition of infection by influenza viruses," Glycobiology, 13(5): 315-326 (2003).
Trouet et al., "A covalent linkage between daunorubicin and proteins that is stable in serum and reversible by lysosomal hydrolases, as required for a lysosomotropic drug-carrier conjugate: In vitro and in vivo studies," Proc. Natl. Acad. Sci. USA 79:626-629, 1982.
Turhan, et al., "Primary role for adherent leukocytes in sickle cell vascular occlusion: A new paradigm," Proceedings of the National Academy of Sciences of the United States of America 99(5):3047-3051, Mar. 5, 2002.
Turner et al., "Molecular Basis of Epithelial Barrier Regulation From Basic Mechanisms to Clinical Application," The American Journal of Pathology, 169(6): 1901-1909 (Dec. 2006).
Tyrrell, D. et al. "Structural requirements for the carbohydrate ligand of E-selectin," PNAS, 88: 10372-10376 (Nov. 1991).
Ueda et. al., "Structure-Activity Relationships of Cyclic Peptide-Based Chemokine Receptor CXCR4 Antagonists: Disclosing the Importance of Side-Chain and Backbone Functionalities," J. Med. Chem. 50:192-198, 2007.
Van Der Velde et al., "Galectin-3 and sST2 in prediction of left ventricular ejection fraction after myocardial infarction," Clinica Chimica Acta, 452, 50-57, Jan. 2016.
Venkataraman et al., "Reawakening Retrocyclins: Ancestral Human Defensins Active Against HIV-1," Plos Biology, 7(4): 720-729 (Apr. 2009).
Wai, "Blockade of Chemokine (C-X-C motif) Receptor 4 for the Inhibition of Hepatocellular Carcinoma Metastasis," A Thesis, in partial fulfillment of requirements for Ph.D. Degree at the Univ. of Hong Kong, Jun. 2008.
Waldmann et al., "Synthesis of 2-Acetamindo-2-Deoxyglucosylasparagine Glyco-Tripeptide and -Pentapeptides by Selective C- and N-Terminal Elongation of the Peptide Chain," Carbohydrate Research 196: 75-93, 1990.
Walker et al., "Rapid Development of Glycan-Specific, Broad, and Potent Anti-HIV-1 gp120 Neutralizing Antibodies in an R5 SIV/HIV Chimeric Virus Infected Macaque," Proceedings of the National Academy of Sciences 108(50):20125-20129, Dec. 2011.
Walsh, "Novel Therapies for Asthma—Advances and Problems," Current Pharmaceutical Design, 11(23): 3027-3038 (2005).
Walz et al., "Recognition by ELAM-1 of the Sialyl-Le.sup.X Determinant on Myeloid and Tumor Cells," Science 250:1132-1135, 1990.
Wang et al., "Binding of High-Mannose-Type Oligosaccharides and Synthetic Oligomannose Clusters to Human Antibody 2G12: Implications for HIV-1 Vaccine Design," Chemistry & Biology 11:127-134, Jan. 2004.
Wang et al., "Effect of ginsenoside rg1 and rh1 on the expression of hla-dr, cd25, cd44, cdIIc and e-selectin on dendritic cell," Zhongguo Mianyixue Zazhi, 23(1): 46-48 (2007)—ABSTRACT.
Wang et al., "Galectin-3 promotes HIV-1 budding via association with Alix and Gag p6," Glycobiology, 24(11), 1022-1035, 2014.
Wang et al., "Targeting the Carbohydrates on HIV-1: Interaction of Oligomannose Dendrons with Human Monoclonal Antibody 2G12 and DC-SIGN," Proceedings of the National Academy of Sciences 105(10):3690-3695, Mar. 2008.
Ward et al., "Blocking of adhesion molecules in vivo as anti-inflammatory therapy," Immunology 1: 165-171, 1994.
Wesche et al., "Characterization of membrane translocation by anthrax protective antigen," Biochemistry, 37(45): 15737-15746 (Nov. 10, 1998).
Whisler et al., "Regulation of Lymphocyte Responses by Human Gangliosides. I. Characteristics of Inhibitory Effects and the Induction of Impaired Activation," Journal of Immunology 125(5):2106-2111, 1980.
Wicklein et al., "E- and P-Selectins Are Essential for Repopulation of Chronic Myelogenous and Chronic Eosinophilic Leukemias in a Scid Mouse Xenograft Model," PLOS One, 8(7), e70139, 2013.
Winkler et al., "Absence of E-selectin at vascular niche delays hematopoietic stem cell turn-over," Blood, 110(11):188A, Nov. 2007.
Winkler et al., "Absence or blockage of E-Selectin-Mediated Cell Adhesion Delays Hematopoietic Stem Cell", ASH Annual Meeting 2009, Abstract #564, Nov. 2009.
Winkler et al., "Absence or blockage of E-Selectin-Mediated Cell Adhesion Delays Hematopoietic Stem Cell", Blood, 114(22), Abstract#564, Dec. 7, 2009.
Winkler et al., "Adhesion of E-selectin promotes growth inhibition and apoptosis of human and murine hematopoietic progenitor cells independent of PSGL-1," Blood, 103(5):1685-92, Mar. 1, 2004.
Winkler et al., "Administration of E-selectin Antagonist GMI-1271 Improves Survival to High-Dose Chemotherapy by Alleviating Mucositis and Accelerating Neutrophil Recovery", Blood, 122(21):2266, Nov. 15, 2013.
Winkler et al., "Administration of E-selectin Antagonist GMI-1271 Improves Survival to High-Dose Chemotherapy by Alleviating Mucositis and Accelerating Neutrophil Recovery", ASH Annual Meeting, Poster #63045, Dec. 8, 2013.
Winkler et al., "Administration of E-Selectin Antagonist GMI-1271 Improves Survival After High-Dose Chemotherapy by Alleviating Mucositis and Accelerating Neutrophil Recovery," Blood, 122(21), Abstract #2266, Nov. 15, 2013.
Winkler et al., "Administration of E-selectin Antagonist GMI-1271 Improves Survival to High-Dose Chemotherapy by Alleviating Mucositis and Accelerating Neutrophil Recovery," Proceedings of the 55$^{th}$ Annual Meeting of the American Society of Hematology, Abstract #2266, Poster Presentation on Dec. 9, 2013, New Orleans, LA.
Winkler et al., "Mobilisation of Reconstituting HSC Is Boosted by Synergy Between G-CSF and E-Selectin Antagonist GMI-1271", Blood, 124(21):317, Dec. 6, 2014.
Winkler et al., "Mobilisation of Reconstituting HSC Is Boosted by Synergy Between G-CSF and E-Selectin Antagonist GMI-1271," Blood, 124(21), Abstract #317, Dec. 6, 2014.
Winkler et al., "Mobilization of CD8$^+$ Central Memory T-Cells with Enhanced Reconstitution Potential in Mice by a Combination of G-CSF and GMI-1271-Mediated E-Selectin Blockade," Blood, 126(23), Abstract #512, Dec. 3, 2015.
Winkler et al., "Mobilization of CD8$^+$ Central Memory T-Cells with Enhanced Reconstitution Potential in Mice by a Combination of G-CSF and GMI-1271-Mediated E-Selectin Blockade," Proceedings of the 57$^{th}$ Annual Meeting of the American Society of Hematology, Abstract #512, Oral Presentation, Dec. 7, 2015, Orlando, FL.
Winkler et al., "Vascular E-Selectin Protects leukemia Cells from Chemotherapy by Directly Activating Pro-Survival NF-Kb Signalling—Therapeutic Blockade of E-Selectin Dampens NF-Kb Activation," Blood, 128(22), Abstract #2823, Dec. 2, 2016.
Winkler et al., "Vascular Niche E-Selectin Protects Acute Myeloid Leukemia Stem Cells from Chemotherapy", Blood, 124(21):620, Dec. 6, 2014.
Winkler et al., "Vascular Niche E-Selectin Protects Acute Myeloid Leukaemia Stem Cells from Chemotherapy," Blood, 124(21), Abstract #620, Dec. 6, 2014.
Winkler et al., "Vascular Niche E-Selectin Regulates Hematopoietic Stem Cell Dormancy, Self Renewal and Chemoresistance", Nature Medicine, doi:10.1038/nm2969, Oct. 21, 2012.
Winkler et al., "Vascular niche E-selectin regulates hematopoietic stem cell dormancy, self renewal and chemoresistance," Nature Medicine, 18(11), 1651-1657, 2012.
Winkler et al., "Vascular niche E-selectin regulates hemopoietic stem cell dormancy, self-renewal and chemoresistance," Nature Medicine, 18(11), 1651-1657, Supplementary Figures and Table, 2012.

(56) References Cited

OTHER PUBLICATIONS

Winkler, "Mobilisation of reconstituting HSC is boosted by E-selectin antagonist GMI-1271," Proceedings of the 56th Annual Meeting of the American Society of Hematology, Abstract #317, Oral Presentation on Dec. 7, 2014, San Francisco, CA.
Winkler, "Vascular bone marrow niches protect AML Leukaemia stem cells from chemotherapy," Proceedings of the 56th Annual Meeting of the American Society of Hematology, Abstract #620, Oral Presentation on Dec. 8, 2014, San Francisco, CA.
Winnard, P. et al,. "Real time non-invasive imaging of receptor-ligand interactions in vivo," J. Cell. Biochem., 90: 454-463 (2003).
Winzer, K. et al. "The Pseudomonas aeruginosa Lectins PA-IL and PA-IIL are Controlled by Quorom Sensing and by RpoS," J. Bacteriol. 182(22): 6401-6411 (2000).
Witz, "The involvement of selectins and their ligands in tumor-progression," Immunol. Lett., 104 (1-2): 89-93 (2006).
Wu et al., "Salivary Agglutinin Inhibits HIV Type 1 Infectivity through Interaction with Viral Glycoprotein 120," AIDS Research and Human Retroviruses, 19(30), 201-209, 2003.
Wu, B. et al. "Structures of the CXCR4 Chemokine GPCR with Small-Molecule and Cyclic Peptide Antagonists," Science, 330(6007): 1066-1071 (Nov. 2010).
Wun et al., "Pan-Selectin Antagonist Rivipansel (GMI-1070) Reduces Soluble E-Selectin Levels While Improving Clinical Outcomes in SCD Vaso-Occlusive Crisis" Blood, 124(21):2704, Dec. 6, 2014.
Xu, J. et al., "Molecular insights and therapeutic targets for diabetic endothelial dysfunction," Circulation, 120: 1266-1286 (2009).
Yamazaki, F. et al,. "Synthesis of an appropriately protected core glycotetraoside, a key intermediate for the synthesis of 'bisected' complex-type glycans of a glycoprotein," Carbohydrate Research 201: 15-30, 1990.
Zeisig et al., "Effect of sialyl Lewis X-glycoliposomes on the inhibition of E-selectin-mediated tumour cell adhesion in vitro" Biochimica et Biophysica Acta (2004) 1660, pp. 31-40.
Zhan et al., "Discovery of Small Molecule CXCR4 Antagonists," J. Med. Chem. 50:5655-5664, 2007.
Zhang et al., "Chemokine CXCL 12 and its receptor CXCR4 expression are associated with perineural invasion of prostate cancer" Journal of Experimental and Clinical Cancer Research (2008) vol. 27 No. 62, pp. 1-9.
Zhang et al., "3790 the Dual E-Selectin/CXCR4 Inhibitor, GMI-1359, Enhances Efficacy of Anti-Leukemia Chemotherapy in FLT3-ITD Mutated Acute Myeloid Leukemia," Blood, 126(23), Abstract #3790, Dec. 3, 2015.
Zhang et al., "The Dual E-selectin/CXCR4 Inhibitor, GMI-1359, Enhances Efficacy of Chemotherapy in FLT3-ITD-Mutated Acute Myeloid Leukemia," Proceedings of the 57th Annual Meeting of the American Society of Hematology, Abstract #3790, Poster Presentation, Dec. 7, 2015, Orlando, FL.
Zhang et al., "The E-selectin/CXCR4 Inhibitor GMI-1359 Effectively Mobilizes Bone Marrow Leukemia Cells and Enhances FLT3 Inhibitor Efficacy in a Murine AML Model," Proceedings of the 107th Annual Meeting of AACR, 3284, Apr. 16-20, 2016, New Orleans, LA.
Zhang, Z. et al. "CXCR4 but not CXCR7 is mainly implicated in ocular leukocyte trafficking during ovalbumin-induced acute uveitis," Experimental Eye Research, 89: 522-531 (2009).
Zhao T. et al. "Targeting human CD34+ hematopoietic stem cells with anti-CD45 × antimyosin light-chain bispecific antibody preserves cardiac function in myocardial infarction" Journal of Applied Physiology, 10(6):1793-1800 (2008).
Zheng, CX et al. "The prognostic value of preoperative serum levels of CEA, CA19-9 and CA72-4 in patients with colorectal cancer," World J. Gastroentero, 7(3): 431-434 (2001).
Zhou et al., "The Selectin GMP-140 Binds to Sialylated, Fucosylated Lactosaminoglycans on Both Myeloid and Nonmyeloid Cells," Journal of Cell Biology 115(2):557-564, 1991.
Zhou, G. et al. "Effect of ET-RA on expression of selectin on the surface of endothelial cell in mice with severe acute pancreatitis," Chongqing Yixue, 35(7): 624-626 (2006)—ABSTRACT.
Zopf et al., "Affinity Purification of Antibodies Using Oligosaccharide-Phenethylamine Derivatives Coupled to Sepharose," Meth. Enzymol. 50:171-175, 1978.
Zuber et al., "Mouse models of human AML accurately predict chemotherapy response," Genes. Dev., 23 (7): 877-889 (2009).
Dutta, P. et al., "Macrophages retain hematopoietic stem cells in the spleen via VCAM-1," J. Exp. Med., 212:497-512 (2015).
Ding L. et al., "Endothelial and perivascular cells maintain haematopoietic stem cells" Nature, 481: 457-462 (2012).
Joshi et al., "Systemic Atherosclerotic Inflammation Following Acute Myocardial Infarction: Myocardial Infarction Begets Myocardial Infarction", Journal of the American Heart Association (2015), 4: e001956, doi: 10.1161/JAHA.115.001956.
Dutta et al., "Myocardial Infarction Accelerates Atherosclerosis", Nature (2012), doi: 10.1038/nature11260.
Dutta et al., "E-Selectin Inhibition Mitigates Splenic HSC Activation and Myelopoiesis in Hypercholesterolemic Mice with Myocardial Infarction", Arterioscler Thromb Vasc. Biol., Sep. 2016; 36(9); 1802-1808.
Nahrendorf et al., "Targeting Splenic Hematopoietic Stem Cells in Cardiovascular Disease", Oncotarget, vol. 6, No. 24, Jul. 21, 2015.
Swirski et al., "Leukocyte Behavior in Atherosclerosis, Myocardial Infarction, and Heart Failure", Science vol. 339, pp. 161-166 (2013), doi: 10.1126/science.1230719.
Thune et al., "Predictors and Prognostic Impact of Recurrent Myocardial Infarction in Patients with Left Ventricular Dysfunction, Heart Failure, or Both Following a First Myocardial Infarction", European Journal of Heart Failure (2011) vol. 13, pp. 148-153, doi: 10.1093/eurjhf/hfq194.

\* cited by examiner

E-Selectin Inhibition Reduces Splenic HSC and Progenitor Proliferation

E-Selectin Inhibition Reduced MI-Induced Myelopoiesis

E-Selectin Inhibition Reduces Inflammation in Atherosclerotic Plaques

E-selectin Inhibition Improved Features of Stable Atherosclerotic Plaques

METHODS FOR THE TREATMENT AND/OR PREVENTION OF CARDIOVASCULAR DISEASE BY INHIBITION OF E-SELECTIN

This application is a United States national stage application filed under 35 U.S.C. § 371 of International Patent Application No. PCT/US2017/020091 accorded an international filing date of Mar. 1, 2017; which claims the benefit under 35 U.S.C. § 119(e) to U.S. Provisional Application No. 62/302,449 filed Mar. 2, 2016, all of which are incorporated by reference herein their entirety.

New methods for treating and/or preventing cardiovascular disease by the use of at least one E-selectin inhibitor and compositions comprising the same are disclosed.

Cardiovascular disease is a leading cause of death and illness in developed counties and an emerging health problem worldwide. (Libby P., *Nature*, 420: 868-874 (2002)). Atherosclerosis, a chronic disease of the arterial wall and important contributor to cardiovascular disease, is a progressive condition effecting large and medium arteries characterized by the accumulation of lipids and inflammatory cells on the inner lining of the artery walls. (Libby P. et al., *Nature*, 473: 317-325 (2011)). This accumulation results in the development of atherosclerotic plaques or lesions. The necrotic breakdown or rupture of unstable plaques results in the exposure of thrombogenic material which can move into the circulation with potentially severe consequences such as myocardial infarction ("heart attack"), unstable angina (accelerating chest pain due to ongoing heart muscle ischemia), sudden cardiac death, and stroke. (Moore K. J. et al., *Cell*, 145: 341-355 (2011)).

The initial steps of atherosclerosis are characterized by the binding of lipid-rich apolipoproteins (lipid carrier proteins) to the arterial lumen. These lipoproteins can enter the subendothelial space and trigger an inflammatory response in the arterial endothelial cells which can trigger monocyte recruitment and attachment to the arterial wall (lumen). (Moore K. J. et al., *Cell*, 145: 341-355 (2011); Yla-Herttuala S. et al., *Proc. Natl. Acad. Sci. USA.*, 88: 5252-5256 (1991)). The process of leukocyte recruitment and tethering to the vascular tissue is mediated by chemokines and selectins. (Galkina E. et al., *Arterioscler. Thromb. Vasc. Biol.*, 27: 2292-2301 (2007)). The upregulation of key adhesion molecules, such as E-selectin, VCAM-1 and ICAM-1, also mediates the process of attachment of monocytes to the arterial lumen. (Cybulsky M. I. et al., *Science*, 251:788-791 (1991)). Once inside, inflammatory monocytes differentiate into macrophages.

In its earliest stages, the atherosclerotic plaque is visible as a fatty streak, characterized by the accumulation of lipids and macrophages which surround the lipids. As the atherosclerotic plaque or lesion progresses, smooth muscle and T cells can also infiltrate the subendothelial space. (Moore K. J. et al., *Cell*, 145: 341-355 (2011), (Libby P., *Nature*, 420: 868-874 (2002)). Macrophages can produce proteases, such as collagenase, that can erode the fibrous caps of the atherosclerotic plaques, leaving these plaques vulnerable to rupture. Vulnerable plaques are characterized by the accumulation of apoptotic cells, resulting in the lipid-filled necrotic core. In addition, a thinning fibrous cap decreases plaque stability, making these atherosclerotic plaques susceptible to rupture, which can result in myocardial infarction (MI).

Recurrent myocardial infarction occurs commonly and has a high mortality rate. (Kaplan R. C. et al., *J. Clin. Epidemiol.*, 55: 654-664 (2002)). For example, one representative trial found that new myocardial ischaemia occurred in 54% of patients within the first year after MI. (Goldstein, J. A. et al., *N. Engl. J. Med.*, 343: 915-922 (2000)). Other studies place the overall risk of re-infarction at one year at 17.4%. (Milonas, C. et al., *Am. J. Cardiol.*, 105: 1229-1234 (2010)). Although the precise reasons for the high frequency of MI recurrence remain unclear, some studies suggest that the ensuing inflammatory response after the initial MI may be responsible. (Dutta P. et al., *Nature*, 487: 325-329 (2012)). After an initial MI, the organism experiences an acute inflammatory event which may exacerbate the pre-existing chronic atherosclerotic disease.

In apolipoprotein E-deficient (apoE-/-) mice, for example, an ischemic event, such as MI or stroke, has been shown to advance atherosclerosis by, for example, increasing the size and instability atherosclerotic plaques. (Dutta P. et al., *Nature*, 487: 325-329 (2012)). Other studies have further suggested that MI aggravates atherosclerosis. (Han Y. et al., *Int. J. Cardiovasc. Imaging*, 30: 253-261 (2014)).

The myeloid cells at the center of this atherosclerotic inflammatory cascade are replenished by hematopoietic stem and progenitor cells (HSPC). (Robbins C. et al., *Circulation*, 125: 364-374 (2012), Leuschner F. et al., *J. Exp. Med.*, 209: 123-137 (2012)). MI diminishes levels of hematopoietic stem cell (HSC) retention factors, triggering HSPC release from the bone marrow. The released HSPC seed the spleen and divide in the presence of stem cell factor to make the myeloid cells that, after being recruited to atherosclerotic plaques, may make the lesions vulnerable to rupture. (Dutta P. et al., *Nature*, 487: 325-329 (2012)).

To further support this hypothesis, studies have demonstrated that the spleens and bone marrow of patients with acute MI showed significantly higher levels of proliferating cells, (Kim E. J. et al., *Circulation Cardiovascular Imaging*, 7: 454-460 (2014), Murphy A. J. et al., *J. Clin. Invest.*, 121: 4138-4149 (2011)), and that these patients showed an increased risk of cardiovascular events. (Emami H. et al., *JACC Cardiovasc. Imaging*, 8: 121-130 (2015)). Thus, splenic HSC activation and proliferation may play an important role in increased atherosclerotic lesion inflammation after MI. However, there is currently no clinically available drug that can block this process. E-selectin, the cell adhesion molecule that plays a role in adhesion of monocytes to arterial endothelial cells, may also regulate HSC proliferation. Nevertheless, the mechanics of HSC proliferation in extramedullary sites such as the spleen is not well understood. (See, e.g., Ding, L. et al., *Nature*, 481: 457-462 (2012), Dutta P. et al., *J. Exp. Med.*, 212: 497-512 (2015)).

Selectins are a group of structurally similar cell surface receptors that are important for mediating leukocyte binding to endothelial cells. These proteins are type 1 membrane proteins and are composed of an amino terminal lectin domain, an epidermal growth factor (EGF)-like domain, a variable number of complement receptor related repeats, a hydrophobic domain spanning region and a cytoplasmic domain. The binding interactions appear to be mediated by contact of the lectin domain of the selectins and various carbohydrate ligands.

There are three known selectins: E-selectin, P-selectin, and L-selectin. E-selectin is found on the surface of activated endothelial cells, which line the interior wall of capillaries. E-selectin binds to the carbohydrate sialyl-Lewis$^x$ (SLe$^x$), which is presented as a glycoprotein or glycolipid on the surface of certain leukocytes (such as monocytes and neutrophils) and helps these cells adhere to capillary walls in areas where surrounding tissue is infected or damaged; and E-selectin also binds to sialyl-Lewis$^a$ (SLe$^a$), which is expressed on many tumor cells. P-selectin is expressed on inflamed endothelium and platelets, and also recognizes SLe$^x$ and SLe$^a$, but also contains a second site that interacts with sulfated tyrosine. The expression of E-selectin and P-selectin is generally increased when the tissue adjacent to a capillary is infected or damaged. L-selectin is expressed on leukocytes. Selectin-mediated intercellular adhesion is an example of a selectin-mediated function.

Modulators of selectin-mediated function include the PSGL-1 protein (and smaller peptide fragments), fucoidan, glycyrrhizin (and derivatives), sulfated lactose derivatives, and heparin. All have shown to be unsuitable for drug development due to insufficient activity, toxicity, lack of specificity, poor ADME characteristics and/or availability of material.

Recently, the role of inflammation in atherosclerosis and its complications has begun to be appreciated. Accordingly, there is a need for new therapies that alleviate the underlying inflammatory cascade and immune cell proliferation/activation responses that contribute to atherosclerotic injury. Disrupting these pathways by modulating E-selectin function may therefore be desirable and lead to new cardiovascular therapies.

The methods of the present invention may have a beneficial therapeutic effect on diseases, disorders and/or conditions where inhibition of E-selectin is useful, including cardiovascular disease.

In some embodiments, the present disclosure is directed to methods for treatment and/or prevention of one cardiovascular disease, the method comprising administering to a subject in need thereof an effective amount of at least one E-selectin inhibitor.

In some embodiments, the present disclosure is directed to methods for treatment and/or prevention of myocardial infarction, the method comprising administering to a subject in need thereof an effective amount of at least one E-selectin inhibitor.

In some embodiments, the present disclosure is directed to methods for treatment and/or prevention of atherosclerosis, the method comprising administering to a subject in need thereof an effective amount of at least one E-selectin inhibitor.

Figure 1:
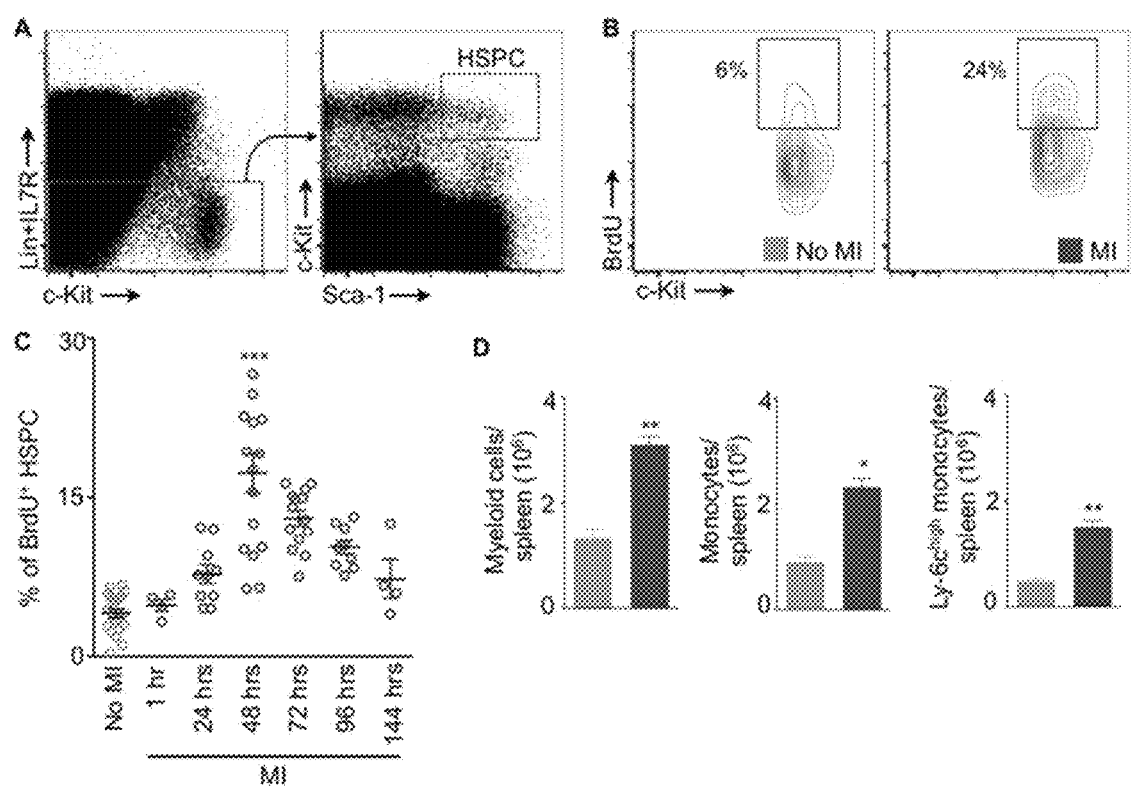
FIG. 1: MI Triggers Splenic HSPC Proliferation. (A) Flow cytometry gating strategy for splenic hematopoietic stem and progenitor cells (HSPC). (B) Representative flow cytometric plots showing BrdU$^+$ splenic HSPC. BrdU was injected 48 hours after myocardial infarction (MI). (C) The graph depicts % of BrdU$^+$ splenic HSPC. BrdU was injected at different time points as indicated on the x axis. (D) Quantified expansion of splenic myeloid cells 4 days after MI. Mean±s.e.m., * P<0.05, ** P<0.01.

Disclosed herein are methods for treating and/or preventing (i.e., inhibiting, decreasing, and/or reducing the likelihood of occurrence in at least one statistical, biological, and/or clinically significant manner) at least one cardiovascular disease, disorder and/or condition where inhibition of E-selectin is useful.

Non-limiting examples of cardiovascular disease include atherosclerosis, myocardial infarction, myocardial ischemia, coronary artery stenosis (occlusion of the coronary arteries), chronic cardiovascular and/or arterial inflammation, acute cardiovascular and/or arterial inflammation, hypercholesterolemia, restenosis (narrowing of the vessel lumen), arrhythmia, thrombosis, hyperlipidemia, hypertension, dyslipoproteinemia, angina (cardiac chest pain), and vascular complications due to a cardiovascular disease (e.g., myocardial infarction or myocardial ischemia).

In some embodiments, the at least one E-selectin inhibitor may be administered prior to or subsequent to an acute cardiovascular event in the subject. In some embodiments, the at least one E-selectin inhibitor may be administered prior to or subsequent to the development or diagnosis of a cardiovascular disease, disorder and/or condition in the subject. In some embodiments, the acute cardiovascular event is a myocardial infarction.

In some embodiments, the present disclosure is directed to methods for treatment and/or prevention of atherosclerosis, the method comprising administering to a subject in need thereof an effective amount of at least one E-selectin inhibitor.

Atherosclerosis generally describes a disease of the arterial blood vessels. As used herein, "atherosclerosis" includes, but is not limited to, chronic and/or acute atherosclerotic inflammation prior to or subsequent to the formation of at least one atherosclerotic plaque in the subject. Atherosclerosis also includes, but is not limited to, chronic progressive atherosclerosis and/or atherosclerotic inflammation. Atherosclerosis also includes, but is not limited to, acute atherosclerosis and/or atherosclerotic inflammation subsequent to an acute vascular event in the subject (such as, for example, myocardial infarction).

In some embodiments, the at least one E-selectin inhibitor may be administered prior to or subsequent to the formation of at least one atherosclerotic plaque, lesion or atheroma in the subject.

In some embodiments, the formation, progression, destabilization and/or rupture of at least one atherosclerotic plaque within the subject is reduced.

Atherosclerotic plaques may be characterized as stable or unstable (i.e., vulnerable to destabilization). Unstable atherosclerotic plaques may be susceptible to disruption or rupture, which exposes thrombogenic material (i.e., thrombi) (e.g., collagen) to the circulation. This can produce interruptions in blood flood (ischemia) in local or distal arteries, which can result in cardiovascular complications, such as, for example, myocardial infarction (MI).

Destabilization of atherosclerotic plaques may occur via many mechanisms. Non-limiting examples of such mechanisms include superficial erosion of the endothelial cells that form the monolayer covering the intima, disruption of the microvessels that form in the atherosclerotic plaque, rupture (i.e., fracture) of the atherosclerotic plaque's fibrous cap, thinning or weakening of the fibrous cap (thus making it susceptible to rupture), and the presence or increase in inflammatory factors that mediate destabilization. (Libby P., *Nature*, 420: 868-874 (2002)).

A non-limiting example of inflammatory factors that mediate destabilization is the presence of inflammatory cells. The progression of atherosclerosis may be associated with systemically increased inflammatory myeloid cells that are recruited to atherosclerotic plaques. (Murphy, A. J. et al., *J Clin. Invest.*, 121: 4138-4149 (2011); Averill, L. E. et al., *Am. J. Pathol.*, 135: 369-377 (1989); Feldman, D. L. et al., *Arterioscler. Thromb.*, 11: 985-994 (1991); Swirski, F. K. et al., *J Clin. Invest.* 117: 195-205 (2007)). The presence of inflammatory myeloid cells may be detrimental to a stable plaque. (Llodra, J. et al., *Proc. Natl. Acad. Sci. U.S.A.*, 101: 11779-11784 (2004)).

Non-limiting examples of destabilization of the at least one atherosclerotic plaque include fractures of the fibrous cap of the atherosclerotic plaque, increases in atherosclerotic plaque size, formation of a necrotic core within the atherosclerotic plaque, increases in size of the necrotic core within the atherosclerotic plaque, reductions in the thickness of the fibrous cap of the atherosclerotic plaque, increases in the number of inflammatory myeloid cells in and around the atherosclerotic plaque, increases in the number of macrophages and foam cells in and around the atherosclerotic plaque, superficial erosions of the endothelial monolayer of the atherosclerotic lesion or plaque, disruptions of the microvessels within the atherosclerotic plaque, increases in the concentration of proteases in and around the atherosclerotic plaque, and causing the atherosclerotic plaques to become vulnerable to rupture.

The presence of a necrotic core in an atherosclerotic plaque may contribute to inflammation, increases the risk of thrombosis and plaque destabilization, and contributes to physical stress on the fibrous cap. (See, e.g., Virmani, R. et al., *J. Interv. Cardiol.*, 15: 439-446 (2002)).

In some embodiments, the stability of at least one atherosclerotic plaque within the subject is increased. Non-limiting examples of stable features of atherosclerotic plaques (i.e., stable phenotype) include smaller plaque size, reduced (i.e., decreased, diminished, smaller) necrotic core size (measured by, for example, necrotic core area), and a thicker fibrous cap of the atherosclerotic plaque. (See, e.g., Moore K. J. et al., *Cell*, 145: 341-355 (2011)).

In some embodiments, the size of at least one atherosclerotic plaque within the subject is decreased. In some embodiments, the necrotic core size of at least one atherosclerotic plaque within the subject is decreased. In some embodiments, the fibrous cap thickness of at least one atherosclerotic plaque within the subject is increased.

In some embodiments, the administration of the at least one E-selectin inhibitor reduces the levels of extramedullary proliferation of hematopoietic stem and/or progenitor cells within the subject. In some embodiments, extramedullary proliferation of hematopoietic stem and/or progenitor cells is reduced in the spleen and/or the liver. Non-limiting examples of extramedullary proliferation of hematopoietic stem and/or progenitor cells include extramedullary hematopoiesis and extramedullary myelopoiesis.

In some embodiments, the administration of the at least one E-selectin inhibitor reduces the number of hematopoietic stem and/or progenitor cells within the subject as measured by flow cytometry.

In some embodiments, the administration of the at least one E-selectin inhibitor reduces the level of extramedullary proliferation of hematopoietic stem cells and/or progenitor cells within the subject by more than 5%, by more than 10%, by more than 15%, by more than 20%, by more than 25%, by more than 30%, by more than 35%, by more than 40%, by more than 45%, by more than 50%, by more than 60%, or by more than 70%, as measured by flow cytometry. In some embodiments, the level of extramedullary proliferation of hematopoietic stem cells and/or progenitor cells in the liver is reduced.

In some embodiments, the administration of at least one E-selectin inhibitor reduces the number of hematopoietic stem and/or progenitor cells within the subject by more than 5%, by more than 10%, by more than 15%, by more than 20%, by more than 25%, by more than 30%, by more than 35%, by more than 40%, by more than 45%, by more than 50%, by more than 60%, or by more than 70%, as measured by flow cytometry. In some embodiments, the number of hematopoietic stem cells and/or progenitor cells in the spleen is reduced.

In some embodiments, the administration of the at least one E-selectin inhibitor reduces the recruitment and/or infiltration of myeloid cells to at least one atherosclerotic plaque within the subject. Non-limiting examples of myeloid cells include monocytes, macrophages, neutrophils, basophils, eosinophils, erythrocytes, dendritic cells, and megakaryocytes and platelets.

In some embodiments, the administration of the at least one E-selectin inhibitor reduces the recruitment and/or infiltration of inflammatory myeloid cells to at least one atherosclerotic plaque within the subject. Non-limiting examples of inflammatory myeloid cells include monocytes, macrophages, neutrophils, basophils, eosinophils, and dendritic cells. Inflammatory myeloid cells, which are involved in the initiation and the progression of atherosclerosis (chronic and acute) and atherosclerotic inflammation, originate from bone marrow-derived progenitor cells.

In some embodiments, the administration of the at least one E-selectin inhibitor reduces the recruitment and/or infiltration of macrophages, neutrophils, and/or monocytes to at least one atherosclerotic plaque within the subject.

In some embodiments, the at least one E-selectin inhibitor is administered after angioplasty, stenting procedure, atherectomy, bypass surgery, or other vessel-corrective techniques.

In some embodiments, the at least one E-selectin inhibitor is administered before angioplasty, stenting procedure, atherectomy, bypass surgery, or other vessel-corrective techniques.

In some embodiments, the administration of the at least one E-selectin inhibitor reduces the number of myeloid cells in the blood of the subject, as measured by flow cytometry, after the subject has suffered a myocardial infarction. In some embodiments, the myeloid cells are inflammatory myeloid cells. In some embodiments, the inflammatory myeloid cells are monocytes, neutrophils and/or macrophages.

In some embodiments, the present disclosure is directed to methods for treatment and prevention of myocardial infarction, the method comprising administering to a subject in need thereof an effective amount of at least one E-selectin inhibitor.

In some embodiments, the subject has previously suffered a myocardial infarction. In some embodiments, the at least one E-selectin inhibitor may be administered before the occurrence of a myocardial infarction in the subject. In some embodiments, the at least one E-selectin inhibitor may be administered after the occurrence of a first or subsequent myocardial infarction in the subject.

In some embodiments, the at least one E-selectin inhibitor is administered to the subject: within one (1) day of the subject suffering a myocardial infarction, within one (1) week of the subject suffering a myocardial infarction, within two (2) weeks of the subject suffering a myocardial infarction, within three (3) weeks of the subject suffering a myocardial infarction, within four (4) weeks of the subject suffering a myocardial infarction, within eight (8) weeks of the subject suffering a myocardial infarction, or within twelve (12) weeks of the subject suffering a myocardial infarction.

In some embodiments, the at least one E-selectin inhibitor inhibits an activity of E-selectin or inhibits the binding of E-selectin to one or more E-selectin ligands (which in turn may inhibit a biological activity of E-selectin).

In some embodiments, the at least one E-selectin inhibitor is chosen from carbohydrate mimetics of an E-selectin ligand, peptides, nucleic acids, antibodies, other antagonists, and prodrugs and pharmaceutically acceptable salts of any of the foregoing.

In some embodiments, the at least one E-selectin inhibitor is chosen from carbohydrate mimetics of an E-selectin ligand, prodrugs thereof, and pharmaceutically acceptable salts of any of the foregoing.

In some embodiments, the at least one E-selectin inhibitor is non-naturally occurring.

In some embodiments, the method comprises administering to the subject in need thereof an effective amount of at least one E-selectin inhibitor chosen from:

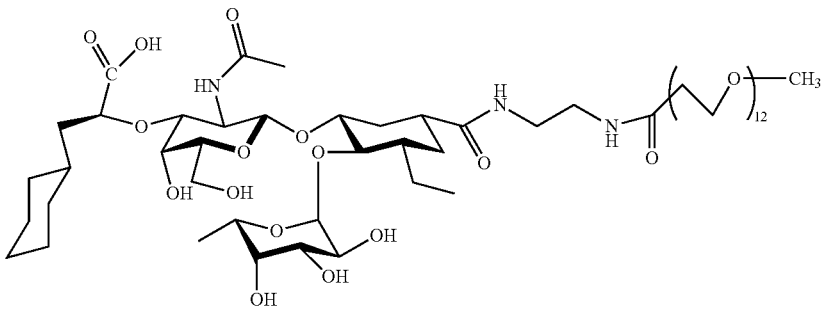

Glycomimetic Compound (I)

prodrugs thereof, and pharmaceutically acceptable salts of any of the foregoing.

The term "at least one" refers to one or more, such as one, two, etc. For example, the term "at least one E-selectin inhibitor" refers to one or more E-selectin inhibitors, such as one E-selectin inhibitor, two E-selectin inhibitors, etc.

The term "antibody" or "antibodies" includes monoclonal antibodies, including isolated, engineered, chemically synthesized or recombinant antibodies (e.g., full length or intact monoclonal antibodies), multispecific antibodies, human antibodies, humanized antibodies (fully or partially humanized), animal antibodies, recombinant antibodies, chimeric antibodies, and antibody fragments exhibiting the desired biological activity.

The term "carbohydrate mimetic" includes any naturally occurring or non-naturally occurring carbohydrate compound in which at least one substituent has been replaced or at least one ring has been modified (e.g., substitution of carbon for a ring oxygen) to yield a compound that is not fully carbohydrate.

The term "E-selectin inhibitor" includes inhibitors of E-selectin only, as well as inhibitors of E-selectin and either P-selectin or L-selectin, and inhibitors of E-selectin, P-selectin, and L-selectin.

The term "hematopoietic stem cells" or "HSCs" includes animal cells, for example mammalian (including human) cells, that have the ability to self-renew and to differentiate into any of several types of blood cells, including red blood cells and white blood cells, including lymphoid cells and myeloid cells. "Self-renewal" includes the ability of cells to divide and generate at least one daughter cell with the identical (e.g., self-renewing) characteristics of the parent cell. The second daughter cell may commit to a particular differentiation pathway. For example, self-renewing hematopoietic stem cells divide and form one daughter stem cell and another daughter cell committed to differentiation in the myeloid or lymphoid pathway. It is well known in the art that hematopoietic stem cells include pluripotent stem cells, multipotent stem cells (e.g., lymphoid stem cells), and/or stem cells committed to specific hematopoietic lineages.

HSCs can also differentiate into endothelial progenitor cells (EPCs). HSCs can include hematopoietic cells having long-term engrafting potential in vivo.

The term "pharmaceutically acceptable salts" includes both acid and base addition salts. Non-limiting examples of pharmaceutically acceptable acid addition salts include chlorides, bromides, sulfates, nitrates, phosphates, sulfonates, methane sulfonates, formates, tartrates, maleates, citrates, benzoates, salicylates, and ascorbates. Non-limiting examples of pharmaceutically acceptable base addition salts include sodium, potassium, lithium, ammonium (substituted and unsubstituted), calcium, magnesium, iron, zinc, copper, manganese, and aluminum salts. Pharmaceutically acceptable salts may, for example, be obtained using standard procedures well known in the field of pharmaceuticals.

The term "prodrug" includes compounds that may be converted, for example, under physiological conditions or by solvolysis, to a biologically active compound described herein. Thus, the term "prodrug" includes metabolic precursors of compounds described herein that are pharmaceutically acceptable. A discussion of prodrugs can be found, for example, in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987. The term "prodrug" also includes covalently bonded carriers that release the active compound(s) as described herein in vivo when such prodrug is administered to a subject. Non-limiting examples of prodrugs include ester and amide derivatives of hydroxy, carboxy, mercapto and amino functional groups in the compound described herein.

The term "progenitor cells" includes cells that can give rise to any one of several different terminally differentiated cell types. These different cell types are usually closely related (e.g. blood cells such as red blood cells, white blood cells and platelets). Progenitor cells are synonymous with the term "multipotent cells." For example, mesenchymal stem cells (also known as marrow stromal cells) are multipotent cells, and are capable of forming osteoblasts, chondrocytes, myocytes, adipocytes, neuronal cells, and β-pancreatic islets cells.

The term "stem cells" includes cells capable of differentiation into other cell types, including those having a particular, specialized function (i.e., terminally differentiated cells, such as erythrocytes and macrophages). Stem cells can be defined according to their source (e.g., adult/somatic stem cells, embryonic stem cells) or according to their potency (e.g., totipotent, pluripotent, multipotent and unipotent).

Biological activity of compounds described herein may be determined, for example, by performing at least one in vitro and/or in vivo study routinely practiced in the art and described herein or in the art. In vitro assays include without limitation binding assays, immunoassays, competitive binding assays and cell based activity assays.

An inhibition assay may be used to screen for antagonists of E-selectin. For example, an assay may be performed to characterize the capability of compounds described herein to inhibit (i.e., reduce, block, decrease, or prevent in a statistically or biologically significant manner) interaction of E-selectin with $sLe^a$ or $sLe^x$. The inhibition assay may be a competitive binding assay, which allows the determination of $IC_{50}$ values. By way of example, E-selectin/Ig chimera may be immobilized onto a matrix (e.g., a multi-well plate, which may be made from polymers, such as polystyrenes; test tubes, and the like); compositions may be added to reduce nonspecific binding (e.g., compositions comprising non-fat dried milk or bovine serum albumin or other blocking buffer routinely used by a person skilled in the art); the immobilized E-selectin may be contacted with the candidate compound in the presence of $sLe^a$ comprising reporter groups under conditions and for a time sufficient to permit $sLe^a$ to bind to the immobilized E-selectin; the immobilized E-selectin may be washed; and the amount of $sLe^a$ bound to immobilized E-selectin may be detected. Variations of such steps can be readily and routinely accomplished by a person of ordinary skill in the art.

Conditions for a particular assay include temperature, buffers (including salts, cations, media), and other components that maintain the integrity of any cell used in the assay and the compound, which a person of ordinary skill in the art will be familiar and/or which can be readily determined. A person of ordinary skill in the art also readily appreciates that appropriate controls can be designed and included when performing the in vitro methods and in vivo methods described herein.

The source of a compound that is characterized by at least one assay and/or technique described herein and/or in the art may be a biological sample that is obtained from a subject who has been treated with the compound. The cells that may be used in the assay may also be provided in a biological sample. A "biological sample" may include samples from a subject, and may be a blood sample (from which serum or plasma may be prepared), biopsy specimens, one or more body fluids (e.g., lung lavage, ascites, mucosal washings, synovial fluid, urine), bone marrow, lymph nodes, tissue explant, organ culture, or any other tissue or cell preparation from the subject or a biological source. Biological samples may further include tissue or cell preparations in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. In some embodiments, the subject or biological source may be human or non-human animal, primary cell culture (e.g., immune cells), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

As understood by a person of ordinary skill in the art, the terms, "treat," "treating" and "treatment," include medical management of a disease, disorder, and/or condition of a subject (i.e., patient, individual) (see, e.g., Stedman's Medical Dictionary). In general, an appropriate dose and treatment regimen provide at least one of the compounds of the present disclosure in an amount sufficient to provide therapeutic and/or prophylactic benefit. For both therapeutic treatment and prophylactic or preventative measures, therapeutic and/or prophylactic benefit includes, for example, an improved clinical outcome, wherein the object is to prevent or slow or retard (lessen) an undesired physiological change or disorder, or to prevent or slow or retard (lessen) the expansion or severity of such disorder. As discussed herein, beneficial or desired clinical results from treating a subject include, but are not limited to, abatement, lessening, or alleviation of symptoms that result from or are associated with the disease, condition, or disorder to be treated; reduced or decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression, including the onset of the disease; amelioration or palliation of the disease state; and remission (whether partial or total), whether detectable or undetectable; and/or overall survival. "Treatment" can include prolonging survival when compared to expected survival if a subject were not receiving treatment.

In some embodiments, the subject is a human. In some embodiments, the subject is a non-human animal. A subject in need of treatment as described herein may exhibit at least one symptom and/or sequelae of a cardiovascular disease, disorder and/or condition or may be at risk of developing a cardiovascular disease, disorder and/or condition. Non-human animals that may be treated include mammals, for example, non-human primates (e.g., monkeys, chimpanzees, gorillas, and the like), rodents (e.g., rats, mice, gerbils, hamsters, ferrets, rabbits), lagomorphs, swine (e.g., pigs, miniature pigs), equines, canines, felines, bovines, and other domestic, farm, and zoo animals. Subjects in need of treatment include those who already have cardiovascular disease, those prone to have or at risk of developing cardiovascular disease, and those in which cardiovascular disease is to be prevented (i.e., decreasing the likelihood of occurrence of the disease, disorder, or condition).

The effectiveness of the compounds of the present disclosure in treating and/or preventing diseases, disorders, and/or conditions treatable by inhibiting an activity of E-selectin can readily be determined by a person of ordinary skill in the relevant art. Determining and adjusting an appropriate dosing regimen (e.g., adjusting the amount of compound per dose and/or number of doses and frequency of dosing) can also readily be performed by a person of ordinary skill in the relevant art. One or any combination of diagnostic methods, including physical examination, assessment and monitoring of clinical symptoms, and performance of analytical tests and methods described herein, may be used for monitoring the health status of the subject.

In some embodiments, the at least one E-selectin inhibitor may be administered as part of a pharmaceutical composition. In some embodiments, the pharmaceutical composition further comprises at least one additional pharmaceutically acceptable ingredient. Such at least one additional pharmaceutically acceptable ingredient may be, for example, an agent (chemical or biological) that promotes recovery, or counteracts side effects of administration of, for example, an antibiotic or corticosteroid.

In pharmaceutical compositions, the at least one E-selectin inhibitor may be administered in the form of a pharmaceutically acceptable derivative, such as a salt, and/or may be used alone and/or in appropriate association, as well as in combination, with other pharmaceutically active compound(s). The combination may be administered sequentially or concurrently. When administration is concurrent, the combination may be administered from a single container or two (or more) separate containers.

An effective amount or therapeutically effective amount includes an amount of at least one compound of the present disclosure or a composition comprising at least one such compound that, when administered to a subject, either as a single dose or as part of a series of doses, is effective to produce at least one desired and/or therapeutic effect. Optimal doses may generally be determined using experimental models and/or clinical trials. Design and execution of preclinical and clinical studies for each of the therapeutics (including when administered for prophylactic benefit) described herein are well within the skill of a person of ordinary skill in the relevant art. The optimal dose of a therapeutic may depend upon the body mass, weight, and/or blood volume of the subject. The minimum dose that is sufficient to provide effective therapy may be used in some embodiments. Subjects may generally be monitored for therapeutic effectiveness using assays suitable for the disease or condition being treated or prevented, which assays will be familiar to those having ordinary skill in the art and are described herein. The level of a compound that is administered to a subject may be monitored by determining the level of the compound (or a metabolite of the compound) in a biological fluid, for example, in the blood, blood fraction (e.g., serum), and/or in the urine, and/or other biological sample from the subject. Any method practiced in the art to detect the compound, or metabolite thereof, may be used to measure the level of the compound during the course of a therapeutic regimen.

The dose of a compound described herein may depend upon the subject's condition, that is, stage of the disease, severity of symptoms caused by the disease, general health status, as well as age, gender, and weight, and other factors apparent to a person of ordinary skill in the medical art. Similarly, the dose of the therapeutic for treating a disease or disorder may be determined according to parameters understood by a person of ordinary skill in the art.

Pharmaceutical compositions described herein may be administered in any manner appropriate to the disease or disorder to be treated as determined by persons of ordinary skill in the medical arts. An appropriate dose and a suitable duration and frequency of administration will be determined by such factors as discussed herein, including the condition of the patient, the type and severity of the patient's disease, the particular form of the active ingredient, and the method of administration. In general, an appropriate dose (or effective dose) and treatment regimen provides the composition(s) as described herein in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail above).

The pharmaceutical compositions described herein may be administered to a subject in need thereof by any one of several routes that effectively delivers an effective amount of the compound. One of ordinary skill in the art is capable of determining the best route of administration. Non-limiting suitable administrative routes include topical, oral, nasal, intrathecal, enteral, buccal, sublingual, transdermal, rectal, vaginal, intraocular, subconjunctival, sublingual, and parenteral administration, including subcutaneous, intravenous and intravascular, intramuscular, intrasternal, intracavernous, intrameatal, intraurethral injection, infusion, and implantation. Implantation includes inserting implantable drug delivery systems (e.g., a stent).

The pharmaceutical compositions described herein may, for example, be sterile aqueous or sterile non-aqueous solutions, suspensions, or emulsions, and may additionally comprise at least one pharmaceutically acceptable excipient (i.e., at least one non-toxic material that does not interfere with the activity of the active ingredient). Such pharmaceutical compositions may, for example, be in the form of a solid, liquid or gas (aerosol). Alternatively, the pharmaceutical compositions described herein may, for example, be formulated as a lyophilizate, and/or compounds described herein may be encapsulated within liposomes using technology known in the art. The pharmaceutical compositions may further comprise at least one additional pharmaceutically acceptable ingredient, which may be biologically active or inactive. Non-limiting examples of such ingredients include buffers (e.g., neutral buffered saline or phosphate buffered saline), carbohydrates (e.g., glucose, mannose, sucrose or dextrans), mannitol, proteins, polypeptides, amino acids (e.g., glycine), antioxidants, chelating agents (e.g., EDTA and glutathione), stabilizers, dyes, flavoring agents, suspending agents, and preservatives.

Any suitable excipient or carrier known to those of ordinary skill in the art for use in compositions may be employed in the compositions described herein. Excipients for therapeutic use are well known, and are described, for example, in Remington: The Science and Practice of Pharmacy (Gennaro, 21st Ed. Mack Pub. Co., Easton, Pa. (2005)). In general, the type of excipient may be selected based on the mode of administration, as well as the chemical composition of the active ingredient(s). Compositions may be formulated for the particular mode of administration. For parenteral administration, pharmaceutical compositions may further comprise water, saline, alcohols, fats, waxes, and buffers. For oral administration, pharmaceutical compositions may further comprise at least one component chosen, for example, from any of the aforementioned ingredients, excipients and carriers, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose, and magnesium carbonate.

The pharmaceutical compositions (e.g., for oral administration or delivery by injection) may be in the form of a liquid. A liquid composition may include, for example, at least one the following: a sterile diluent such as water for injection, saline solution, such as physiological saline, Ringer's solution, isotonic sodium chloride, fixed oils that may serve as a solvent and/or suspending medium, polyethylene glycols, glycerin, propylene glycol and/or other solvents; antibacterial agents; antioxidants; chelating agents; buffers and agents for the adjustment of tonicity such as sodium chloride and dextrose. A parenteral preparation can be enclosed in ampoules, disposable syringes or multiple dose vials made of glass or plastic. In some embodiments, the pharmaceutical composition comprises physiological saline. In some embodiments, the pharmaceutical composition is an injectable composition, and in some embodiments, the injectable composition is sterile.

For oral formulations, at least one of the compounds of the present disclosure can be used alone or in combination with at least one additive appropriate to make tablets, powders, granules and/or capsules, for example, those chosen from conventional additives, disintegrators, lubricants, diluents, buffering agents, moistening agents, preservatives, coloring agents, and flavoring agents. The pharmaceutical compositions may be formulated to include at least one buffering agent, which may provide for protection of the active ingredient from low pH of the gastric environment and/or an enteric coating. A pharmaceutical composition may be formulated for oral delivery with at least one flavoring agent, e.g., in a liquid, solid or semi-solid formulation and/or with an enteric coating.

Oral formulations may be provided as gelatin capsules, which may contain the active compound or biological along with powdered carriers. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract.

A pharmaceutical composition may be formulated for sustained or slow release. Such compositions may generally be prepared using well known technology and administered by, for example, oral, rectal or subcutaneous implantation, or by implantation at the desired target site. Sustained-release formulations may contain the active therapeutic dispersed in a carrier matrix and/or contained within a reservoir surrounded by a rate controlling membrane. Excipients for use within such formulations are biocompatible, and may also be biodegradable; the formulation may provide a relatively constant level of active component release. The amount of active therapeutic contained within a sustained release formulation depends upon the site of implantation, the rate and expected duration of release, and the nature of the condition to be treated and/or prevented.

The pharmaceutical compositions described herein can be formulated as suppositories by mixing with a variety of bases such as emulsifying bases or water-soluble bases. The pharmaceutical compositions may be prepared as aerosol formulations to be administered via inhalation. The pharmaceutical compositions may be formulated into pressurized acceptable propellants such as dichlorodifluoromethane, propane, nitrogen and the like.

The compounds of the present disclosure and pharmaceutical compositions comprising at least one such compound may be administered topically (e.g., by transdermal administration). Topical formulations may be in the form of a transdermal patch, ointment, paste, lotion, cream, gel, and the like. Topical formulations may include one or more of a penetrating agent or enhancer (also call permeation enhancer), thickener, diluent, emulsifier, dispersing aid, or binder. Physical penetration enhancers include, for example, electrophoretic techniques such as iontophoresis, use of ultrasound (or "phonophoresis"), and the like. Chemical penetration enhancers are agents administered either prior to, with, or immediately following administration of the therapeutic, which increase the permeability of the skin, particularly the stratum corneum, to provide for enhanced penetration of the drug through the skin. Additional chemical and physical penetration enhancers are described in Transdermal Delivery of Drugs, A. F. Kydonieus (ED) 1987 CRL Press; Percutaneous Penetration Enhancers, eds. Smith et al. (CRC Press, 1995); Lennerãs et al., J. Pharm. Pharmacol. 54:499-508 (2002); Karande et al., Pharm. Res. 19:655-60 (2002); Vaddi et al., Int. J. Pharm. 91:1639-51 (2002); Ventura et al., J. Drug Target 9:379-93 (2001); Shokri et al., Int. J. Pharm. 228(1-2):99-107 (2001); Suzuki et al., Biol. Pharm. Bull. 24:698-700 (2001); Alberti et al., J. Control Release 71:319-27 (2001); Goldstein et al., Urology 57:301-5 (2001); Kiijavainen et al., Eur. J. Pharm. Sci. 10:97-102 (2000); and Tenjarla et al., Int. J. Pharm. 192: 147-58 (1999).

Kits comprising unit doses of at least one compound of the present disclosure, for example in oral or injectable doses, are provided. Such kits may include a container comprising the unit dose, an informational package insert describing the use and attendant benefits of the therapeutic in treating the pathological condition of interest, and/or optionally an appliance or device for delivery of the at least one compound of Formula (I) and/or pharmaceutical composition comprising the same.

EXAMPLE

Materials and Methods

Mice:

The study was approved by the local institutional animal care and use committee (IACUC). Apolipoprotein E-deficient mice (ApoE$^{-/-}$) (C57BL/6 genetic background, Jackson Laboratory) were used for this study. Mice were kept in a 22° C. room with a 12 hour light/dark cycle and received water ad libitum. To induce atherosclerosis, mice were fed a cholesterol rich, high fat diet for 5 weeks (Harlan Teklad, 42% calories from fat). Coronary ligation was performed as described below to artificially induce a myocardial infarction.

After coronary ligation, mice were kept on a cholesterol rich, high fat diet for another three weeks. Simultaneously, mice were treated with Glycomimetic Compound (I) at 20 mg/kg body weight twice a day subcutaneously. Control mice were treated with PBS. After three weeks of treatment, mice were sacrificed, blood was drawn via cardiac puncture in 50 mM EDTA (Sigma-Aldrich), organs were harvested and immediately process in DPBS buffer containing 0.5% of bovine serum albumin and 1% fetal bovine serum. Red blood cells were lysed with 1×RBC lysis buffer (Biolegend).

Aorta was excised under a microscope (Carl Zeiss) and minced in digestion buffer (450 U/ml collagenase I, 125 U/ml collagenase XI, 60 U/ml DNase I, and 60 U/ml hyaluronidase (Sigma-Aldrich)). Aortic tissue was incubated at 37° C. for 1 hour and then filtered through a 40 µm nylon cell strainer (Falcon).

Cholesterol Determination:

Plasma cholesterol levels were determined with a commercially available enzymatic colorimetric assay (Cholesterol E, Wako Diagnostics).

Coronary Ligation:

Mice were randomly assigned to either coronary ligation or the control group. Mice received preoperatively buprenorphin 0.05 mg/kg body weight. Mice were intubated and anesthetized with 2% isoflurane. Depth of anesthesia was assessed by toe pinch. The fur over the left thorax was shaved, mice were placed on a heating pad (37° C.) and skin was disinfected with betadine and an alcohol wipe. The mice had been put on a ventilator before thoracotomy was carried out at the fourth left intercostal space. Pericardium was removed, and the left anterior descending coronary artery was identified and ligated with a monofilament 7-0 nylon suture to induce MI. The thorax was closed with a 5-0 suture, and the skeletal muscles as well as skin were closed with absorbable sutures. Buprenorphin twice daily was continued for three days after the procedure. The wound was monitored daily and proper recovery after surgery was ensured.

Flow Cytometry:

An LSRII flow cytometer was used for flow cytometry experiments. Aortic and splenic tissues were filtered through 40 µm cell strainer and diluted in 300 µl FACS buffer to obtain a single cell suspension. Staining with fluorochrome-labelled antibodies was done in 5 ml falcon tubes (BD Bioscience).

The following antibodies were used to analyze myeloid and lymphoid cells in blood: Ly6c FITC, CD115 PerCp-Cy5.5, CD11b APC-Cy7, Ly6g APC, CD3 BV421 and CD19 BV605. Ly6c positive monocytes were identified as CD19$^-$, CD3$^-$, CD11b$^+$, CD115$^+$, Ly6g$^-$ and Ly6c$^+$. Blood neutrophils were identified as CD19$^-$, CD3$^-$, CD11b$^+$, CD115$^-$, Ly6g$^+$.

To determine myeloid cells in aortic tissue, two staining steps were used. First, a phycoerythrin (PE) anti-mouse lineage antibody mix containing antibodies binding CD90 (clone 53-2.1), B220, CD49b, NK1.1 and Ter-119 were used. In a second step antibodies against the following marker were applied: F4/80 PE-Cy7, CD11b APC-Cy7, Ly6g APC and Ly6c FITC. Monocytes were identified as lineage$^-$, CD11b$^+$, Ly6g$^-$, and F4/80$^-$. Neutrophils were identified as lineage$^-$, CD11b$^+$ and Ly6g$^+$. lineage$^-$, CD11b$^+$, Ly6g$^-$, and F4/80$^+$ cells in atherosclerotic plaques were considered as macrophages.

Additional antibodies were used to stain for hematopoietic stem and progenitor cells in the spleen. Besides the lineage antibodies used to stain myeloid cells, we added PE-conjugated antibodies binding CD11b, CD11c, B220, Ly-6G and IL7Rα to the lineage master mix. In a second staining step, we used antibodies directed against c-kit, Sca-1, CD16/32, CD34, and CD115. Hematopoietic stem and progenitors cells (HSPC) were identified as lineage$^-$, c-kit$^+$ and Sca-1$^+$. HSPC that are CD48$^-$ and CD150$^+$ were considered as hematopoietic stem cells (HSC).

Granulocyte and macrophage progenitors were identified as lineage$^-$, c-kit$^+$, Sca-1$^+$, CD16/32$^{high}$ and CD34$^{high}$.

For cell cycle analysis, Ki-67 in BV605 and propidium iodide were used. Proliferating cells were identified as Ki-67$^{high}$ and propidium iodide$^{high}$.

Histology:

Aortic roots were embedded in O.C.T. medium (Sakura Finetek), snap-frozen 2-methyl butane and stored at −80° C. Aortic roots were cut with a Leica cryostat, and sections of 5 µm thickness were used for histology. CD11b staining was performed in order to determine myeloid cell accumulation in the atherosclerotic plaque. Sections were stained with anti-CD11b antibody (clone M1/70, BD Biosciences). A biotinylated anti-rat antibody served as secondary antibody (Vector Laboratories, Inc.) VECTA STAIN ABC kit (Vector Laboratories, Inc.). AEC substrate (DakoCytomation) was applied for color reaction. Accumulation of myeloid cells in atherosclerotic plaques and plaque size were quantified with iVision software. Masson Trichrome staining (Sigma Aldrich) was used to stain for necrotic cores and fibrous caps in atherosclerotic plaques. Necrotic core area was analyzed by measuring the total acellular area per atherosclerotic plaque. In order to measure fibrous cap thickness, at least 3 measurements of the thinnest fibrous cap within one atherosclerotic plaque were taken and averaged. Quantification of necrotic cores as well as fibrous cap thickness were performed using iVision software after scanning the stained sections with NanoZoomer 2.0-RS (Hamamatsu).

Magnetic Resonance Imaging:

To evaluate the safety of E-selectin inhibition and to rule out unwanted effects on cardiac functions, we analyzed left ventricular function on day 1 and day 21 after coronary ligation using magnetic resonance imaging (MRI). A 7 Tesla horizontal bore Pharmascan (Bruker) that is attached to a custom-made mouse cardiac coil (Rapid Biomedical) was used to take cine images of the left ventricular short axis. Analysis and quantification were done using software Segment (http://segment.heiberg.se).

Results

Myocardial Infarction Triggers Splenic HSPC Proliferation:

To investigate the time course of upstream splenic HSPC (FIG. 1A) proliferation after MI, we ligated the left anterior descending coronary artery. At different time points after MI, we injected the mice with BrdU, a thymidine analogue that can be incorporated into DNA strands during the S phase of cell cycle. We found splenic HSPC proliferation progressively increased after coronary ligation. It peaked on day 3 and returned to steady-state level on day 7 (FIG. 1B). On day 2 after coronary ligation, HSPC proliferation was more than 4 times higher than in mice without coronary ligation (control, 4.06±0.4; day 3 after coronary ligation, 17.3±1.9). Concomitantly, splenic myeloid cell numbers increased at day 7 after myocardial ischemia (FIG. 1C), thereby indicating that proliferating HSPC differentiated into myeloid cells.

Figure 2:
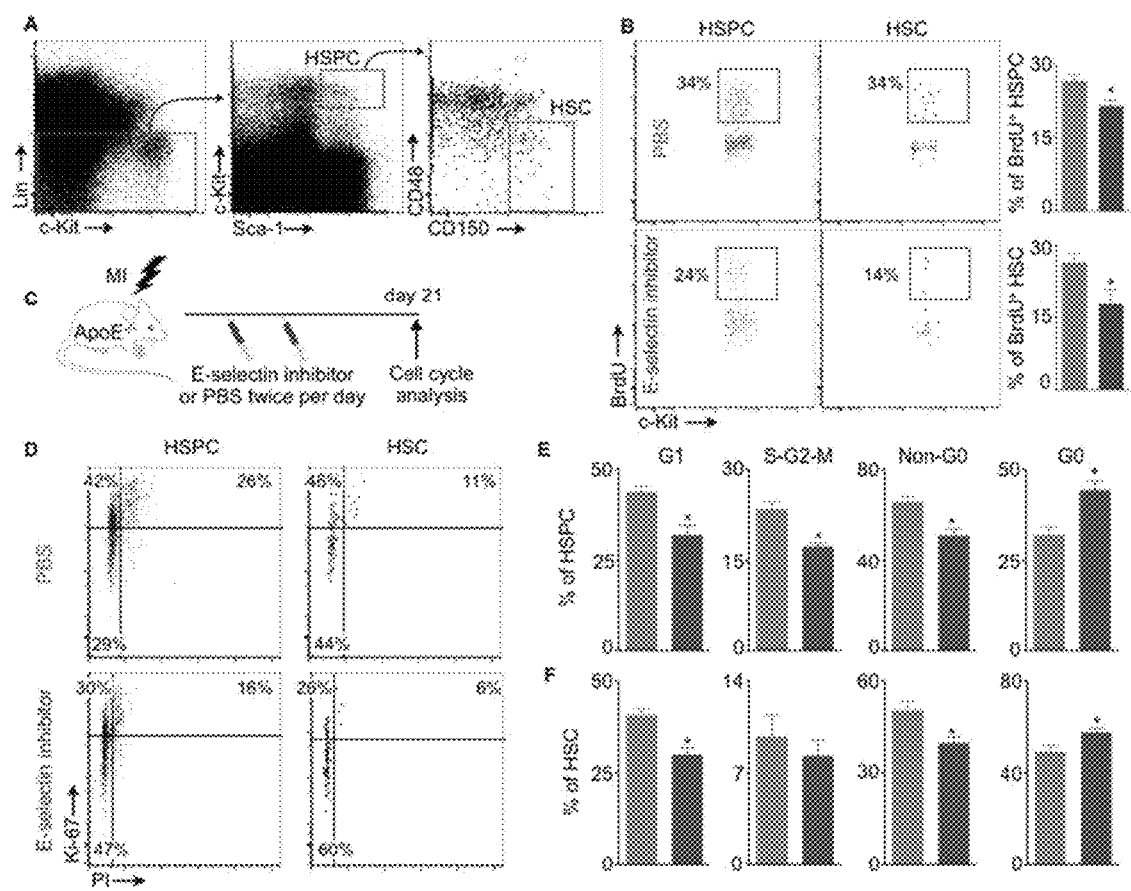
FIG. 2: E-Selectin Inhibition Reduces Splenic HSC and Progenitor Proliferation. (A) HSC gating strategy. (B) % of BrdU$^+$ HSPC and HSC in the spleens of C57BL/6 mice. BrdU was injected 48 hours after coronary ligation. (C) Experimental design to investigate the effects of E-selectin inhibitor on HSPC and HSC proliferation in atherosclerotic mice with MI. (D) Representative flow cytometric plots depicting HSPC and HSC proliferation after MI in ApoE$^{-/-}$ mice treated with either PBS or E-selectin inhibitor. (E) % of splenic HSPC in different phases of the cell cycle. Mean±s.e.m., * P<0.05. (F) % of splenic HSC in different phases of the cell cycle. Mean±s.e.m., * P<0.05.

E-Selectin Reduces Splenic HSC and Progenitor Proliferation:

Splenic HSC and progenitor proliferation leads to extramedullary myelopoiesis 16. However, the regulation of splenic HSC (FIG. 2A) proliferation is not well understood. Since E-selectin expressed by bone marrow sinusoidal endothelial cells promotes HSC proliferation 17, we hypothesized that inhibiting E-selectin would reduce splenic HSC proliferation. To test this hypothesis, we treated C57BL/6 mice with an E-selectin inhibitor after coronary ligation. This resulted in significant decreased HSC (PBS, 26.4±1.7; E-selectin inhibitor, 17.6±3.2) and HSPC (PBS, 26.5±1.1; E-selectin inhibitor, 21.3±3.9) proliferation in the spleen (FIG. 2B).

To investigate the role of E-selectin in splenic HSC proliferation in atherosclerotic mice, we performed coronary ligation in ApoE$^{-/-}$ mice fed a high-fat diet. Following MI, the mice received E-selectin inhibitor injections. Cell cycle analysis was done on day 21 after myocardial ischemia (FIG. 2C). HSPC and HSC were stained for Ki-67, an antigen expressed during the cell cycle. DNA marking with PI distinguished cells in S-G2-M phase (i.e. proliferating cells) from those in G1 phase (FIG. 2D). We found that E-selectin inhibition decreased the percentage of HSPC in G1, S-G2-M and Non-G0 phases, whereas the percentage of HSPC in G0 stage was increased (FIG. 2E). We detected similar effects on splenic HSC proliferation (FIG. 2F). Interestingly, bone marrow HSC and HSPC proliferation was unchanged (data not shown).

Figure 3:
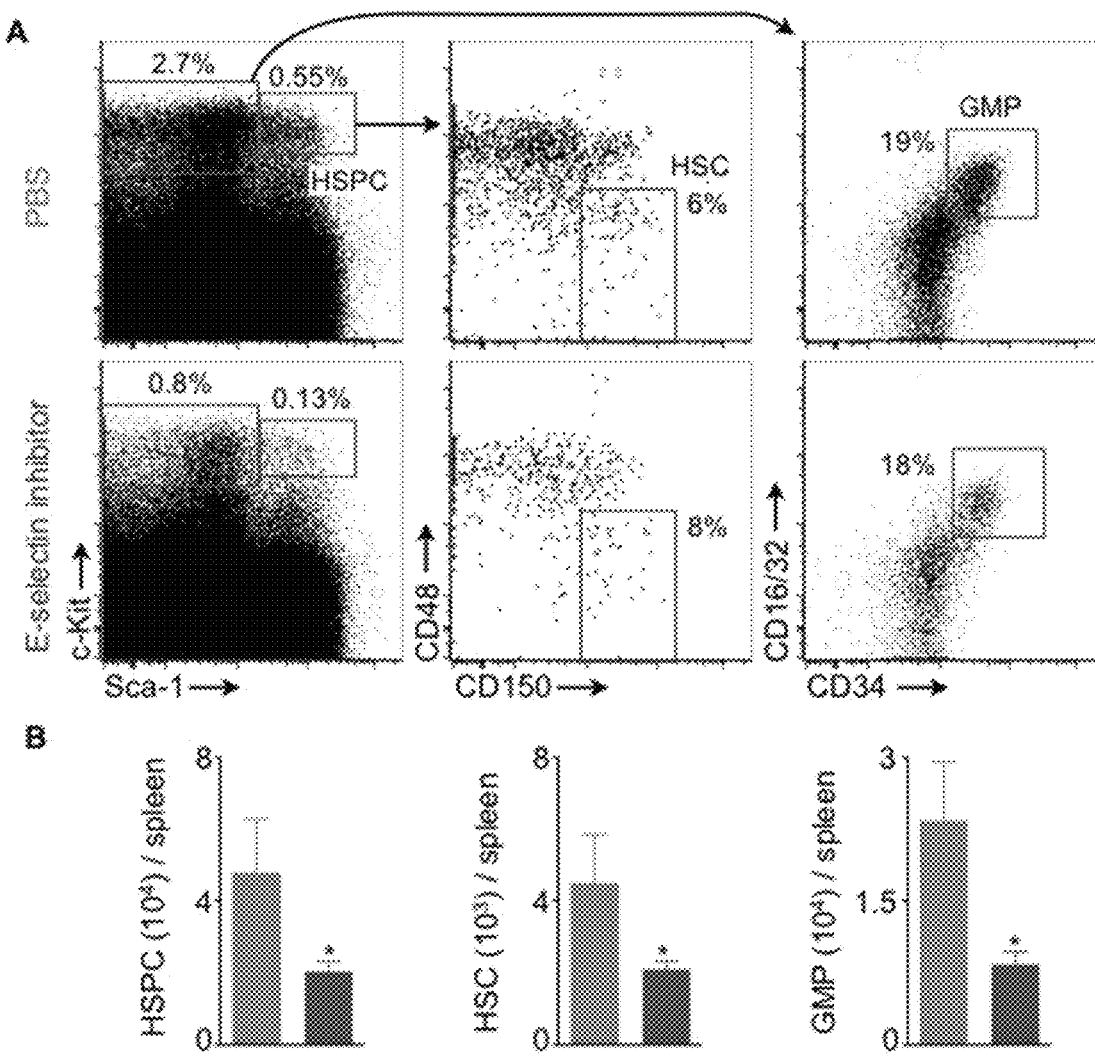
FIG. 3: E-Selectin Inhibition Reduces Splenic HSC and Progenitor Numbers. (A) Flow cytometric gating strategy for splenic HSC and granulocyte and macrophage progenitors (GMP). (B) Quantification of HSPC, HSC and GMP in the spleens of ApoE$^{-/-}$ mice 3 weeks after coronary ligation. The mice were treated with either PBS or E-selectin inhibitor twice a day for 3 weeks. Mean±s.e.m., * P<0.05.

E-Selectin Inhibition Reduced Splenic HSC and Progenitor Numbers:

Since inhibiting E-selectin decreased HSC and HSPC proliferation after MI, we investigated whether the treatment also decreased their numbers. FIG. 3A depicts the gating strategy for HSPC (Lin− c-Kit+ Sca-1+), HSC (Lin− c-Kit+ Sca-1+ CD48− CD150+) and granulocyte monocyte progenitors (GMP) (Lin− c-Kit+ Sca-1− CD16/32+ CD34+). In steady state, the spleen harbors very few HSC and progenitors (HSC, 666±166; HSPC, 3400±1,030; GMP, 1300±337 per spleen). However, after MI, splenic HSC and HSPC greatly multiplied (FIGS. 3A & 3B). E-selectin inhibition significantly mitigated the expansion of HSPC (PBS, 47,572±15; 125; E-selectin inhibitor, 20,174±2,876), HSC (PBS, 4,486±1,334; E-selectin inhibitor, 2,085±237) and GMP (PBS, 23,339±6,179; E-selectin inhibitor, 8,323±1, 334) populations (FIG. 3B).

Figure 4:
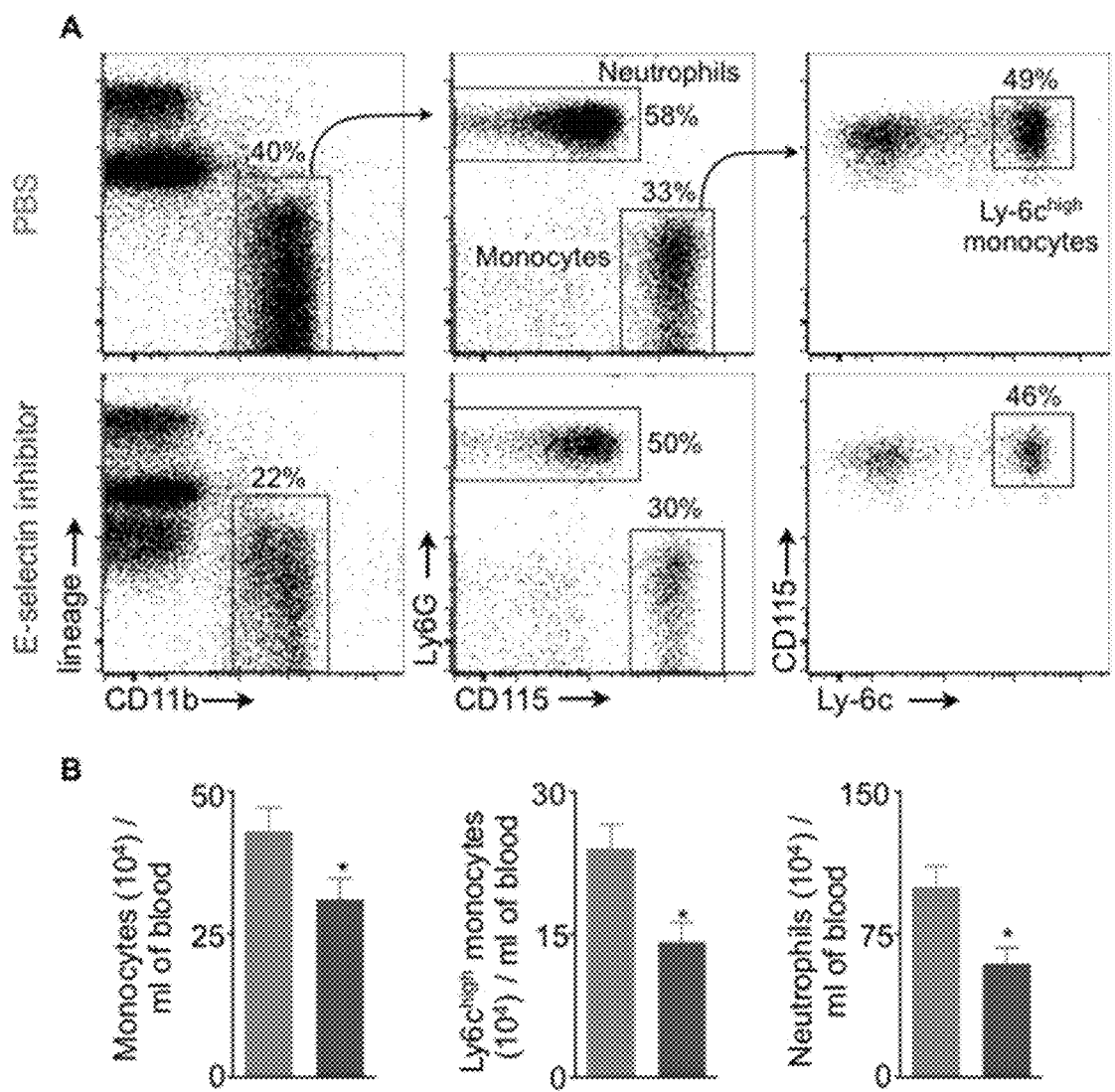
FIG. 4: E-Selectin Inhibition Reduced MI-Induced Myelopoiesis (Blood leukocytosis). (a) flow cytometric gating strategy for neutrophils, monocytes and Ly-6c$^{high}$ monocytes. The flow cytometric plots depict % of myeloid cells in the blood of ApoE$^{-/-}$ mice treated with either PBS or E-selectin inhibitor. (B) Enumeration of neutrophils, monocytes and Ly-6c$^{high}$ monocytes in ApoE$^{-/-}$ mice 3 weeks after MI. Mean±s.e.m., * P<0.05.

E-Selectin Inhibition Reduced MI-Induced Myelopoiesis:

Since E-selectin inhibition significantly reduced HSC and HSPC proliferation and number in the spleen, we hypothesized the treatment would also reduce circulating myeloid cell numbers after MI. Indeed, E-selectin inhibition significantly reduced myeloid cell numbers in the blood (FIGS. 4A & 4B), indicating their less production at the extramedullary site. FIG. 4A shows the gating strategy for monocyte, Ly-6chigh monocytes and neutrophils. E-selectin inhibition curbed their expansion after MI by 28%, 41% and 40%, respectively (FIG. 4B).

Figure 5:
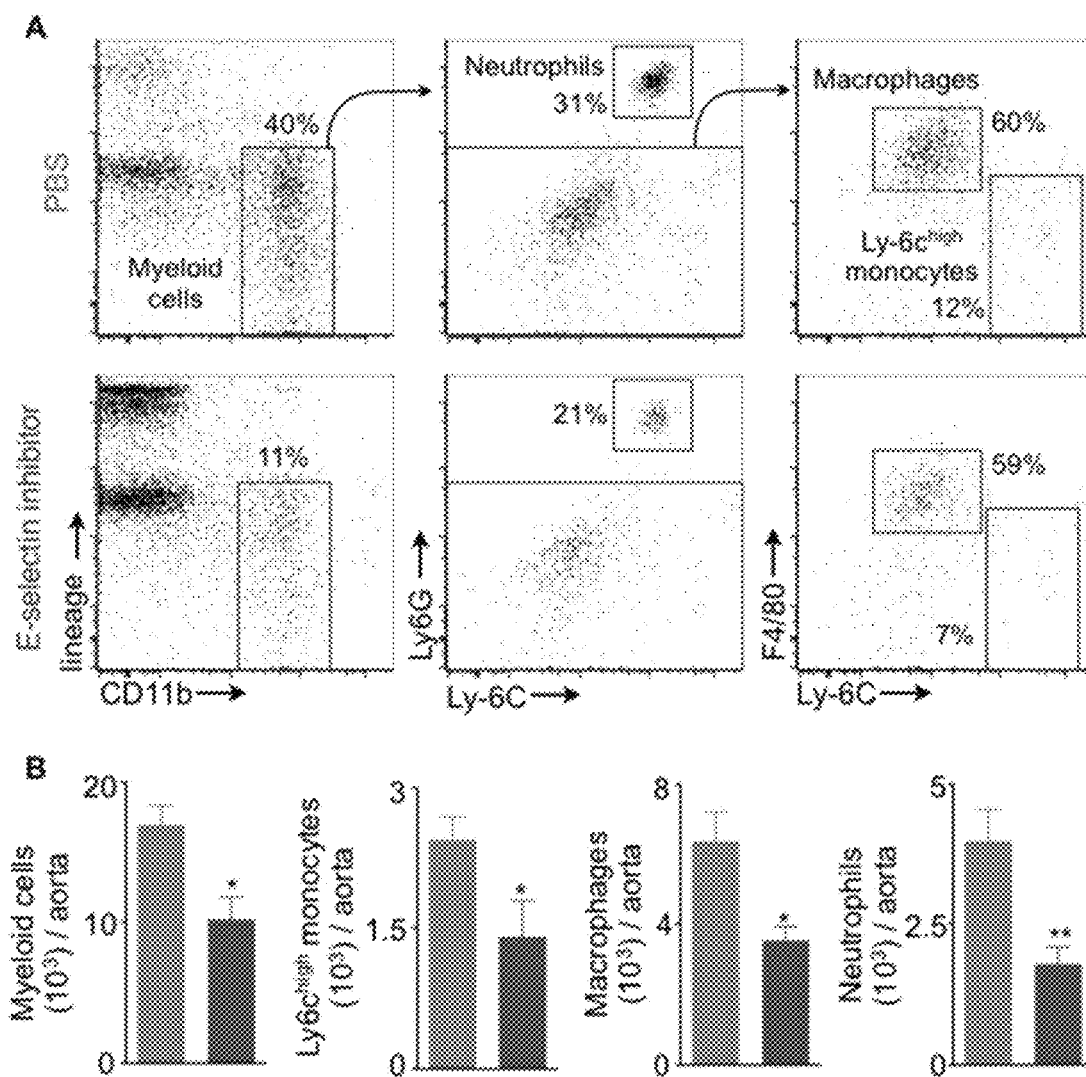
FIG. 5: E-Selectin Inhibition Reduces Inflammation in Atherosclerotic Plaques. E-selectin inhibition mitigates inflammation in atherosclerotic plaques. Aortas were excised from ApoE$^{-/-}$ mice fed a high-fat diet 3 weeks after coronary ligation. (A) The flow cytometric plots depict gating strategy and % of different myeloid cells in the aorta. (B) Quantification of aortic myeloid cells, Ly-6c$^{high}$ monocytes, macrophages and neutrophils. Mean±s.e.m., * P<0.05, ** P<0.01.
Figure 6:
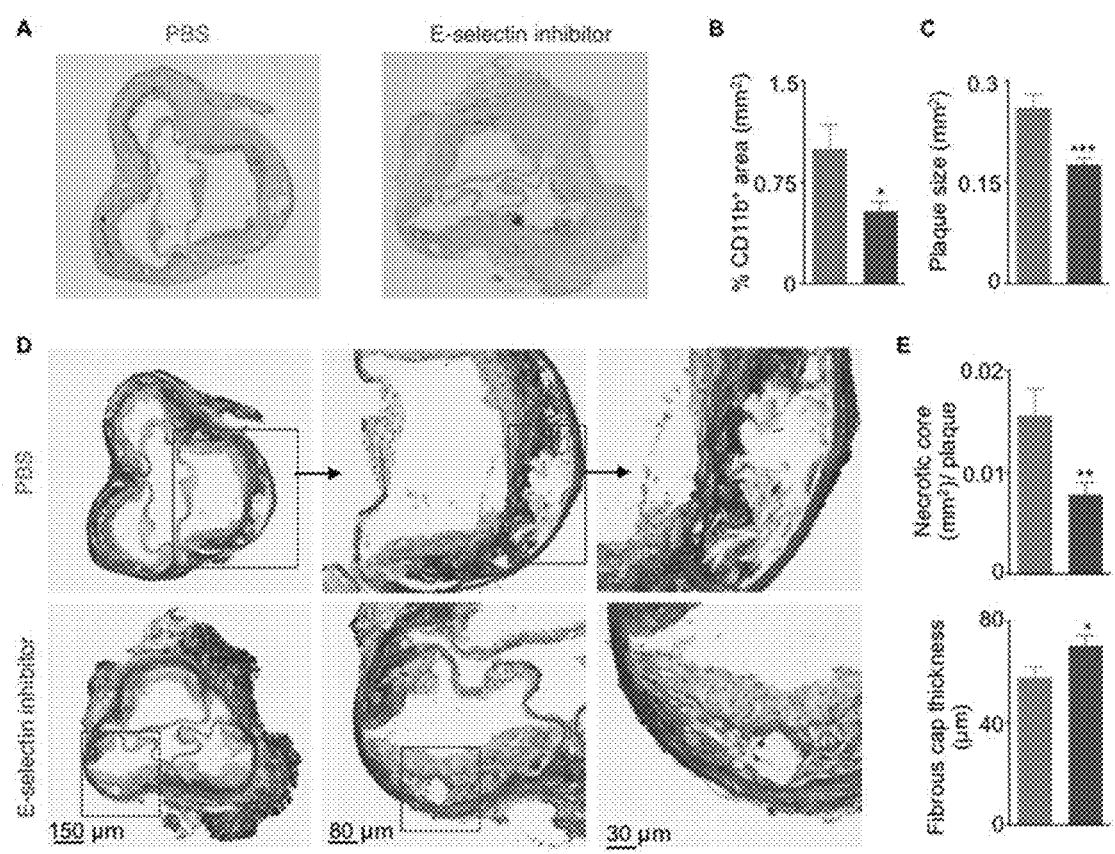
FIG. 6: E-selectin Inhibition Improved Features of Stable Atherosclerotic Plaques. Representative images (A) and quantification (B) of CD11b$^+$ area in aortic root sections. (C) Quantification of plaque size after E-selectin inhibitor treatment. Representative images (D) and quantification (E) of necrotic core area and fibrous cap thickness in aortic root sections. Mean±s.e.m., * P<0.05,  P<0.01, * P<0.001.

E-Selectin Inhibition Reduces Inflammation in Atherosclerotic Plaques and Enhances Stable Atherosclerotic Plaque Phenotype:

Atherosclerosis is associated with systemically increased inflammatory myeloid cells that are recruited to atherosclerotic plaques. The presence of inflammatory cells is detrimental to a stable plaque. MI exacerbates atherosclerosis by augmenting myeloid cell supply to the aorta. Since E-selectin inhibitor can effectively curb MI-induced myelopoiesis (FIG. 4), it might reduce inflammation in atherosclerotic lesions, thus promoting stable plaques. To this end, we induced MI in ApoE−/− mice fed a high-fat diet. The mice were injected with either PBS or E-selectin inhibitor for 3 weeks after infarction. E-selectin inhibition significantly reduced the accumulation of myeloid cells, Ly-6chigh monocytes, macrophages and neutrophils in the aorta (FIGS. 5A & 5B). Diminished inflammation in the lesions was confirmed by histology showing a smaller CD11b-stained area in sections of the aortic root (FIGS. 6A & 6B). Furthermore, plaque size in the aortic root was significantly decreased (FIG. 6C).

Matrix metalloproteinases produced by inflammatory myeloid cells erode the fibrous cap, thereby allowing blood to come into contact with highly thrombogenic materials in the underlying necrotic core. This leads to acute coronary thrombosis and myocardial ischemia. Accordingly, using E-selectin inhibitor treatment to reduce inflammation in atherosclerotic lesions might promote stable plaque features such as small necrotic cores and thick fibrous caps. To test this, we performed Masson staining of aortic root sections from ApoE−/− mice 3 weeks after MI. We found that E-selectin inhibition significantly reduced necrotic core area and increased fibrous cap thickness (FIGS. 6D & 6E), results that indicate more stable plaques.

What is claimed is:

1. A method for treating atherosclerosis and/or myocardial infarction in a subject in need thereof that has suffered a myocardial infarction, the method comprising administering to a subject in need thereof that has suffered a myocardial infarction an effective amount of at least one E-selectin inhibitor, wherein the at least one E-selectin inhibitor is chosen from

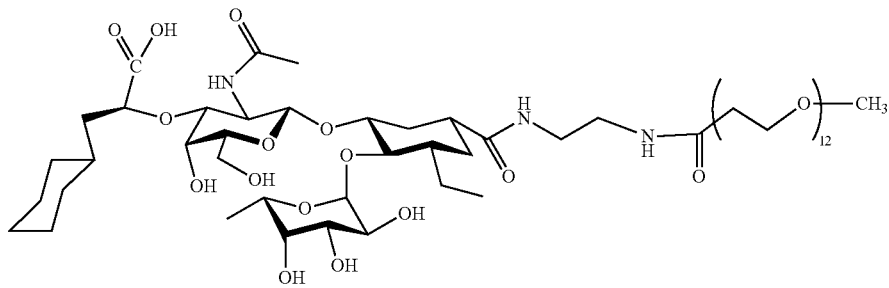

Glycomimetic Compound (I)

prodrugs thereof, and pharmaceutically acceptable salts of any of the foregoing.

2. The method according to claim 1, wherein the subject suffered a myocardial infarction within 12 weeks prior to said administration.

3. The method according to claim 1, wherein formation, progression, destabilization, and/or rupture of at least one atherosclerotic plaque within the subject is reduced.

4. The method according to claim 1, wherein the size of at least one atherosclerotic plaque within the subject is decreased.

5. The method according to claim 1, wherein the stability of at least one atherosclerotic plaque within the subject is increased.

6. The method according to claim 5, wherein the necrotic core size of at least one atherosclerotic plaque within the subject is decreased.

7. The method according to claim 5, wherein the fibrous cap thickness of at least one atherosclerotic plaque within the subject is increased.

8. The method according to claim 1, wherein the level of extramedullary proliferation of hematopoietic stem or progenitor cells within the subject is reduced.

9. The method according to claim 8, wherein the level of extramedullary proliferation of hematopoietic stem or progenitor cells within of the subject is reduced by more than 5%, more than 10%, more than 20%, more than 30%, or more than 40% as measured by flow cytometry.

10. The method according to claim 1, wherein the number of hematopoietic stem or progenitor cells within the subject is reduced.

11. The method according to claim 10, wherein the number of hematopoietic stem or progenitor cells within the subject is reduced by more than 5%, more than 10%, more than 20%, more than 30%, or more than 40% as measured by flow cytometry.

12. The method according to claim 1, wherein the number of myeloid cells in the subject's blood after a myocardial infarction is reduced.

13. The method according to claim 12, wherein the myeloid cells in the subject's blood after a myocardial infarction comprise inflammatory myeloid cells.

14. The method according to claim 13, wherein the inflammatory myeloid cells are chosen from monocytes, neutrophils, and macrophages.

15. The method of claim 1, wherein the method treats atherosclerosis in the subject.

16. The method of claim 1, wherein the method treats a myocardial infarction in the subject.

17. The method of claim 1, wherein the method treats atherosclerotic inflammation in the subject.

18. The method of claim 1, wherein the method treats acute atherosclerotic inflammation.

19. The method of claim 1, wherein the method treats chronic atherosclerotic inflammation.

20. The method of claim 1, wherein the method treats atherosclerotic inflammation prior to the formation of at least one atherosclerotic plaque in the subject.

21. The method of claim 1, wherein the method treats atherosclerotic inflammation subsequent to the formation of at least one atherosclerotic plaque in the subject.

22. A method for treating an acute inflammatory event in a subject in need thereof that has suffered a myocardial infarction, the method comprising administering to a subject in need thereof that has suffered a myocardial infarction an effective amount of at least one E-selectin inhibitor, wherein the at least one E-selectin inhibitor is chosen from

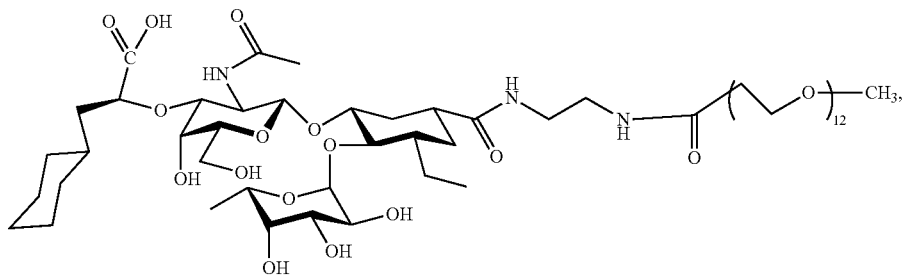

Glycomimetic Compound (I)

prodrugs thereof, and pharmaceutically acceptable salts of any of the foregoing.

23. The method of claim 22, wherein immune cell proliferation and/or activation responses that contribute to atherosclerotic injury in the subject are reduced.

* * * * *